US010214525B2

(12) United States Patent
Koenemann et al.

(10) Patent No.: US 10,214,525 B2
(45) Date of Patent: Feb. 26, 2019

(54) CHLORINATED NAPTHALENETETRACARBOXYLIC ACID DERIVATIVES, PREPARATION THEREOF AND USE THEREOF IN ORGANIC ELECTRONICS

(71) Applicant: BASF SE, Ludwigshafen (DE)

(72) Inventors: Martin Koenemann, Mannheim (DE); Gabriele Mattern, Schifferstadt (DE); Frank Wuerthner, Hoechberg (DE); Cornelia Goepfert, Schwetzingen (DE); Ruediger Schmidt, Paderborn (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/334,743

(22) Filed: Oct. 26, 2016

(65) Prior Publication Data

US 2017/0174676 A1 Jun. 22, 2017

Related U.S. Application Data

(62) Division of application No. 12/479,228, filed on Jun. 5, 2009, now Pat. No. 9,512,354.

(60) Provisional application No. 61/116,760, filed on Nov. 21, 2008.

(30) Foreign Application Priority Data

Jun. 6, 2008 (DE) .................. 10 2008 027 214

(51) Int. Cl.
| | |
|---|---|
| *C07D 209/76* | (2006.01) |
| *C07D 471/02* | (2006.01) |
| *C07D 471/06* | (2006.01) |
| *C07D 491/06* | (2006.01) |
| *C07D 493/06* | (2006.01) |
| *C09K 11/06* | (2006.01) |
| *H01L 51/00* | (2006.01) |
| *C07D 487/02* | (2006.01) |
| *C09B 57/08* | (2006.01) |
| *H01L 51/05* | (2006.01) |
| *H01L 51/42* | (2006.01) |
| *H01L 51/50* | (2006.01) |

(52) U.S. Cl.
CPC ......... *C07D 471/02* (2013.01); *C07D 471/06* (2013.01); *C07D 487/02* (2013.01); *C07D 491/06* (2013.01); *C07D 493/06* (2013.01); *C09B 57/08* (2013.01); *C09K 11/06* (2013.01); *H01L 51/0053* (2013.01); *H01L 51/0545* (2013.01); *H01L 51/42* (2013.01); *H01L 51/50* (2013.01); *Y02E 10/549* (2013.01)

(58) Field of Classification Search
USPC .............. 524/89; 546/65, 26, 70; 257/40, 53
See application file for complete search history.

(56) References Cited

U.S. PATENT DOCUMENTS

| | | | |
|---|---|---|---|
| 4,368,319 A | 1/1983 | Hocker et al. | |
| 4,461,922 A | 7/1984 | Gay et al. | |
| 6,198,091 B1 | 3/2001 | Forrest et al. | |
| 6,198,092 B1 | 3/2001 | Bulovic et al. | |
| 6,451,415 B1 | 9/2002 | Forrest et al. | |
| 6,864,396 B2 | 3/2005 | Smith et al. | |
| 2003/0100779 A1 | 5/2003 | Vogel et al. | |
| 2003/0153005 A1 | 8/2003 | Schmid et al. | |
| 2004/0046182 A1 | 3/2004 | Chen et al. | |
| 2004/0130776 A1 | 7/2004 | Ho et al. | |
| 2005/0098726 A1 | 5/2005 | Peumans et al. | |
| 2005/0176970 A1 | 8/2005 | Marks et al. | |
| 2005/0224905 A1 | 10/2005 | Forrest et al. | |
| 2005/0238974 A1 | 10/2005 | Sekiya et al. | |
| 2006/0202195 A1 | 9/2006 | Marks et al. | |
| 2007/0190783 A1 | 8/2007 | Gomez et al. | |
| 2008/0009092 A1 | 1/2008 | Koenemann et al. | |
| 2008/0035914 A1 | 2/2008 | Konemann et al. | |
| 2008/0300405 A1* | 12/2008 | Konemann ......... | C07D 471/06 544/245 |
| 2009/0078312 A1 | 3/2009 | Konemann et al. | |
| 2009/0166614 A1 | 7/2009 | Könemann et al. | |
| 2009/0301552 A1 | 12/2009 | Koenemann et al. | |
| 2011/0042651 A1* | 2/2011 | Koenemann ......... | C07D 221/14 257/40 |

FOREIGN PATENT DOCUMENTS

| | | |
|---|---|---|
| DE | 36 20 332 A1 | 12/1987 |
| DE | 37 03 131 A1 | 8/1988 |
| DE | 101 48 172 A1 | 4/2003 |
| DE | 10 2004 014 046 A1 | 9/2004 |
| EP | 0 033 015 A1 | 8/1981 |

(Continued)

OTHER PUBLICATIONS

Hiroto Tachikawa, et al., "Hybrid Density Functional Theory (DFT) Study on Electronic States of Halogen-Substituted Organic-Inorganic Hybrid Compounds: Al-NTCDA", Japanese Journal of Applied Physics, vol. 44, No. 6A, XP002429103, Jun. 10, 2005, pp. 3769-3773.

Brooks A. Jones, et al., "Tuning Orbital Energetics in Arylene Diimide Semiconductors. Materials Design for Ambient Stability of n-Type Charge Transport", JACS Articles, J. AM. Chem. Soc., Nov. 14, 2007, pp. A-T.

Kevin C. See, et al., "Easily Synthesized Naphthalene Tetracarboxylic Diimide Semiconductors with High Electron Mobility in Air", Chem, Mater., 20, May 10, 2008, pp. 3609-3616.

(Continued)

*Primary Examiner* — Monique R Peets
(74) *Attorney, Agent, or Firm* — Oblon, McClelland, Maier & Neustadt, L.L.P.

(57) ABSTRACT

The present invention relates to chlorinated naphthalenetetracarboxylic acid derivatives, preparation thereof and use thereof as charge transport materials, exciton transport materials or emitter materials.

7 Claims, 2 Drawing Sheets

(56) References Cited

FOREIGN PATENT DOCUMENTS

| | | |
|---|---|---|
| EP | 0 249 841 A1 | 12/1987 |
| EP | 1 445 115 A1 | 8/2004 |
| JP | 63-201188 | 8/1988 |
| JP | 2-255789 | 10/1990 |
| JP | 5-27469 | 2/1993 |
| JP | 11-149948 | 6/1999 |
| WO | 00/70655 A2 | 11/2000 |
| WO | 2005/019373 A2 | 3/2005 |
| WO | 2007/074137 A1 | 7/2007 |
| WO | 2007/093643 A1 | 8/2007 |
| WO | 2007/116001 A2 | 10/2007 |
| WO | 2009/024512 A1 | 2/2009 |

OTHER PUBLICATIONS

Christoph Thalacker et al., "Synthesis and Optical and Redox Properties of Core-Substituted Naphthalene Diimide Dyes", Journal of Organic Chemistry, vol. 71, 2006, pp. 8098-8105.

Antonio Facchetti et al., "Gate Dielectrics for Organic Field-Effect Transistors: New Opportunities for Organic Electronics", Advanced Materials, vol. 17, 2005, pp. 1705-1725.

R. A. Laudise et al., "Physical Vapor Growth of Organic Semiconductors", Journal of Crystal Growth, vol. 187, 1998, pp. 449-454.

Ch. Kloc et al., "Physical Vapor Growth of Centimeter-Sized Crysals of α-Hexathiophene", Journal of Crystal Growth, vol. 182, 1997, pp. 416-427.

Héctor A. Becerril et al., "High-Performance Organic Thin-Film Transistors through Solution-Sheared Deposition of Small-Molecule Organic Semiconductors", Advanced Materials, vol. 20, 2008, pp. 2588-2594.

C. W. Tang, "Two-Layer Organic Photovoltaic Cell", Applied Physics Letter, vol. 48, No. 2, Jan. 13, 1986, pp. 183-185.

N. Karl et al., "Efficient Organic Photovoltaic Cells", Molecular Crystals and Liquid Crystals, vol. 252. 1994, pp. 243-258.

Christoph J. Brabec et al., "Plastic Solar Cells", Advanced Functional Materials, vol. 11, No. 1, Feb. 2001, pp. 15-26.

Peter Peumans et al., "Small Molecular Weight Organic Thin-Film Photodetectors and Solar Cells", Journal of Applied Physics, vol. 93, No. 7, Apr. 1, 2003. Pages 3693-3723.

J. Drechsel et al., "High Efficiency Organic Solar Cells Based on Single or Multiple PIN", Thin Solid Films, vols. 451-452, 2004, pp. 515-517.

* cited by examiner

CHLORINATED NAPTHALENETETRACARBOXYLIC ACID DERIVATIVES, PREPARATION THEREOF AND USE THEREOF IN ORGANIC ELECTRONICS

This application is a divisional application of U.S. Ser. No. 12/479,228 filed on Jun. 5, 2009 which claims priority to U.S. 61/116,760 filed on Nov. 21, 2008.

The present invention relates to chlorinated naphthalenetetracarboxylic acid derivatives, preparation thereof and use thereof as charge transport materials, exciton transport materials or emitter materials.

It is expected that, in the future, not only the classical inorganic semiconductors but increasingly also organic semiconductors based on low molecular weight or polymeric materials will be used in many sectors of the electronics industry. In many cases, these organic semiconductors have advantages over the classical inorganic semiconductors, for example better substrate compatibility and better processibility of the semiconductor components based on them. They allow processing on flexible substrates and enable their interface orbital energies to be adjusted precisely to the particular application sector by the methods of molecular modeling. The significantly reduced costs of such components have brought a renaissance to the field of research of organic electronics. "Organic electronics" is concerned principally with the development of new materials and manufacturing processes for the production of electronic components based on organic semiconductor layers. These include in particular organic field-effect transistors (OFETs) and organic light-emitting diodes (OLEDs), and photovoltaics. Great potential for development is ascribed to organic field-effect transistors, for example in memory elements and integrated optoelectronic devices. Organic light-emitting diodes (OLEDs) exploit the property of materials of emitting light when they are excited by electrical current. OLEDs are particularly of interest as alternatives to cathode ray tubes and liquid-crystal displays for producing flat visual display units. Owing to the very compact design and the intrinsically lower power consumption, devices which comprise OLEDs are suitable especially for mobile applications, for example for applications in cellphones, laptops, etc. Great potential for development is also ascribed to materials which have maximum transport widths and high mobilities for light-induced excited states (high exciton diffusion lengths) and which are thus advantageously suitable for use as an active material in so-called excitonic solar cells. It is generally possible with solar cells based on such materials to achieve very good quantum yields.

H. Tachikawa and H. Kawabata describe, in Jpn. J. Appl. Phys., volume 44, No. 6A (2005), p. 3769-3773, hybrid density functional theory studies on complexes of halogenated naphthalene-1,8:4,5-tetracarboxylic bisanhydrides. In these studies, the effects of the halogen substitution on the electronic states were exclusively computer-modeled. A performable synthesis of halogenated naphthalene-1,8:4,5-tetracarboxylic bisanhydrides and measurements on real existing compounds are not described.

DE 36 20 332 describes 2,3,6,7-tetrachloronaphthalene-1,4,5,8-tetracarboxylic dianhydride and 2,3,6,7-tetrachloronaphthalene-1,4,5,8-tetracarboxylic dimide and a process for preparing these compounds.

DE 37 03 131 A1 describes 2,3,6,7-tetrafluoronaphthalene-1,8:4,5-tetracarboxylic bisimides, processes for preparation thereof and use thereof for preparing radical anion salts with electrical conductivity.

DE 101 48 172 A1 describes fluorescent naphthalene-1,8:4,5-tetracarboximides with electron-donating substituents in the 2 and 6 position on the ring and the use thereof as fluorescent dyes, for coloring high molecular weight organic and inorganic materials, as laser dyes, for fluorescent marking and as a fluorescent label for biomolecules.

JP 11149984 describes organic electroluminescence devices containing a layer based on at least one of the following compounds:

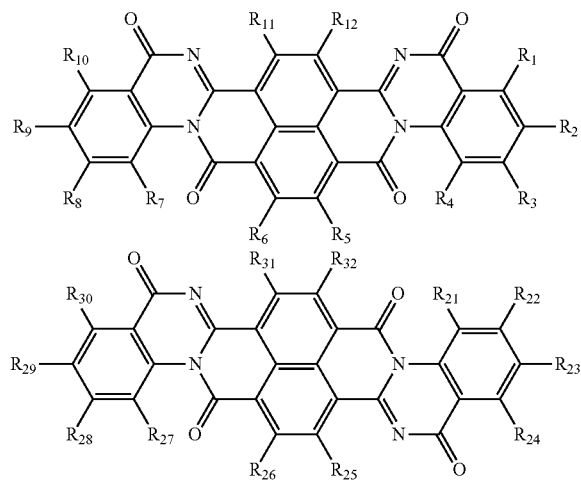

wherein $R_1$ to $R_{12}$ and $R_{21}$ to $R_{32}$, respectively, represent i.a. a hydrogen atom, a halogen atom, an alkyl group, a cycloalkyl group, an alkoxy group, an annular alkoxy group or a substituted or unsubstituted aryl group.

B. A. Jones, A. Facchetti, M. R. Wasilewski and T. J. Marks describe, in JACS ARTICLES, published on Web Nov. 14, 2007, structural and electronic criteria for the stability of n-semiconductors under ambient conditions. Also mentioned are cyanated naphthalenetetracarboxylic acid derivatives, though the mobilities achieved are still in need of improvement.

US 2005/0176970 A1 describes n-semiconductors based on substituted perylene-3,4-dicarboximides and perylene-3,4:9,10-bis(dicarboximides). This document also describes, in quite general terms and without any proof by a preparation example, substituted naphthalene-1,8-dicarboximides and naphthalene-1,4,5,8-bis(dicarboximides) and use thereof as n-semiconductors.

K. C. See, C. Landis, A. Sarjeant and H. E. Katz describe, in Chem. Mater. 2008, 20, 3609-3616, semiconductors based on the following two compounds:

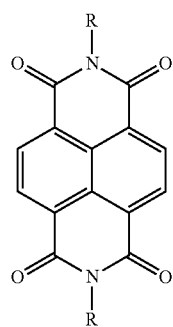

-continued

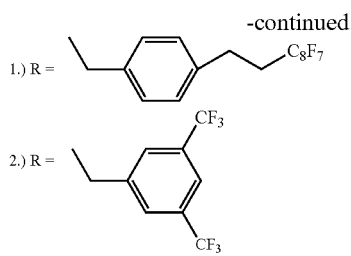

WO 2007/074137 describes compounds of the general formula (A)

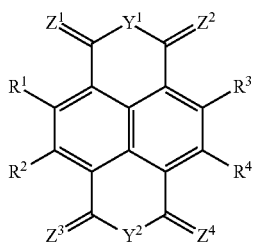

where
at least one of the $R^1$, $R^2$, $R^3$ and $R^4$ radicals is a substituent which is selected from Br, F and CN,
$Y^1$ is O or $NR^a$ where $R^a$ is hydrogen or an organyl radical,
$Y^2$ is O or $NR^b$ where $R^b$ is hydrogen or an organyl radical,
$Z^1$ and $Z^2$ are each independently O or $NR^c$ where $R^c$ is an organyl radical,
$Z^3$ and $Z^4$ are each independently O or $NR^d$ where $R^d$ is an organyl radical,
where, in the case that $Y^1$ is $NR^a$ and at least one of the $Z^1$ and $Z^2$ radicals is $NR^c$, $R^a$ with an $R^c$ radical may also together be a bridging group having from 2 to 5 atoms between the flanking bonds,
where, in the case that $Y^2$ is $NR^b$ and at least one of the $Z^3$ and $Z^4$ radicals is $NR^d$, $R^b$ with an $R^d$ radical may also together be a bridging group having from 2 to 5 atoms between the flanking bonds,
and the use thereof as n-semiconductors in organic field-effect transistors.

WO 2007/093643 describes the use of compounds of the general formula (B)

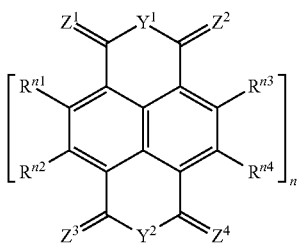

where
n is 2, 3 or 4,
at least one of the $R^{n1}$, $R^{n2}$, $R^{n3}$ and $R^{n4}$ radicals is fluorine, if appropriate at least one further $R^{n1}$, $R^{n2}$, $R^{n3}$ or $R^{n4}$ radical is a substituent which is independently selected from Cl and Br, and the remaining radicals are each hydrogen,
$Y^1$ is O or $NR^a$ where $R^a$ is hydrogen or an organyl radical,
$Y^2$ is O or $NR^b$ where $R^b$ is hydrogen or an organyl radical,
$Z^1$, $Z^2$, $Z^3$ and $Z^4$ are each O,
where, in the case that $Y^1$ is $NR^a$, one of the $Z^1$ and $Z^2$ radicals may also be $NR^c$, where the $R^a$ and $R^c$ radicals together are a bridging group,
where, in the case that $Y^2$ is $NR^b$, one of the $Z^3$ and $Z^4$ radicals may also be $NR^d$, where the $R^b$ and $R^d$ radicals together are a bridging group,
as semiconductors, especially n-semiconductors, in organic electronics, especially for organic field-effect transistors, solar cells and organic light-emitting diodes.

European patent application 07114556.9, unpublished at the priority date of the present application, describes the use of compounds of the general formula (C)

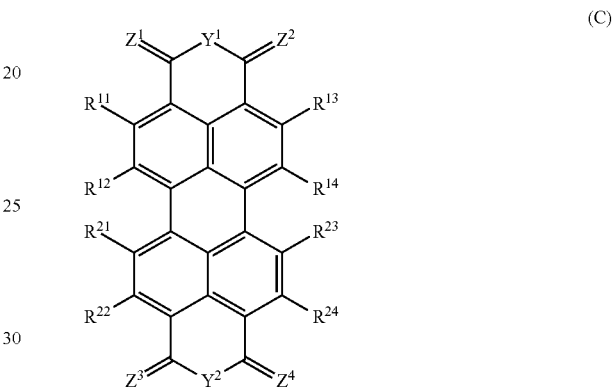

in which
$Y^1$ is O or $NR^a$ where $R^a$ is hydrogen or an organyl radical,
$Y^2$ is O or $NR^b$ where $R^b$ is hydrogen or an organyl radical,
$Z^1$, $Z^2$, $Z^3$ and $Z^4$ are each O,
the $R^{11}$, $R^{12}$, $R^{13}$, $R^{14}$, $R^{21}$, $R^{22}$, $R^{23}$ and $R^{24}$ radicals are each chlorine and/or fluorine,
where 1 or 2 of the $R^{11}$, $R^{12}$, $R^{13}$, $R^{14}$, $R^{21}$, $R^{22}$, $R^{23}$ and $R^{24}$ radicals may also be CN and/or 1 $R^{11}$, $R^{12}$, $R^{13}$, $R^{14}$, $R^{21}$, $R^{22}$, $R^{23}$ and $R^{24}$ radical may also be hydrogen, and
where, in the case that $Y^1$ is $NR^a$, one of the $Z^1$ and $Z^2$ radicals may also be $NR^c$, where the $R^a$ and $R^c$ radicals together are a bridging X group,
where, in the case that $Y^2$ is $NR^b$, one of the $Z^3$ and $Z^4$ radicals may also be $NR^d$, where the $R^b$ and $R^d$ radicals together are a bridging X group,
as emitter materials, charge transport materials or exciton transport materials. Likewise described is the preparation of the chlorinated compounds, wherein the chlorination is brought about by reaction with chlorine in chlorosulfonic acid and in the presence of catalytic amounts of iodine.

There is still a need for semiconductor materials which are advantageously suitable for use in organic electronics, specifically for field-effect transistors and organic solar cells. What are being sought are especially semiconductor materials which are virtually transparent in the visible wavelength range, especially in the wavelength range above 450 nm. Preferably, the semiconductor materials have absorption of less than 10%, in particular no absorption, in the wavelength range above 450 nm, which are air-stable and have high charge mobilities. Likewise, what are being sought are especially semiconductor materials which are processible in liquid form; i.e. the semiconductor materials should be sufficiently soluble, which permits wet processing directly and allows the fabrication of low-cost organic electronics.

Preferably, e.g. the semiconductor materials should have charge mobilities of least 0.1 cm² V⁻¹ s⁻¹ when deposited by vacuum-deposition methods or e.g. of least 0.01 cm² V⁻¹ s⁻¹ when deposited in liquid form.

It has now been found that, surprisingly, chlorinated naphthalenetetracarboxylic acid derivatives are particularly advantageously suitable as charge transport materials, exciton transport materials or emitter materials. They are notable especially as n-type semiconductors with high charge mobilities preferably e.g. of at least 0.01 cm² V⁻¹ s⁻¹. In addition, the components resulting therefrom are air-stable.

The invention therefore firstly provides for the use of compounds of the general formula (I)

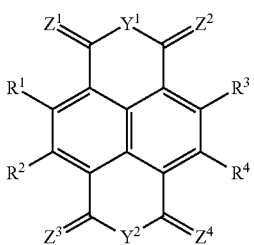

(I)

where at least two of the R¹, R², R³ and R⁴ radicals are Cl and the remaining radicals are hydrogen, Y¹ is O or NR$^a$ where R$^a$ is hydrogen or an organyl radical, Y² is O or NR$^b$ where R$^b$ is hydrogen or an organyl radical, Z¹ and Z² are each O, Z³ and Z⁴ are each O.

as charge transport materials, exciton transport materials or emitter materials. They are notable especially as charge transport materials.

The invention further provides compounds of the general formula (I)

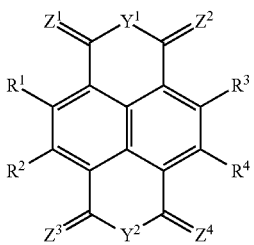

(I)

where

R¹, R² and R³ are each Cl and R⁴ is hydrogen, or R¹, R², R³ and R⁴ are each Cl,

Z¹, Z², Z³, Z⁴ are each O and Y¹ and Y² are each as defined above and in detail below, except of 2,3,6,7-tetrachloronaphthalene-1,4,5,8-tetracarboxylic dianhydride and 2,3,6,7-tetrachloronaphthalene-1,4,5,8-tetracarboxylic diimide.

The invention further provides compounds of the formula (I.Ba)

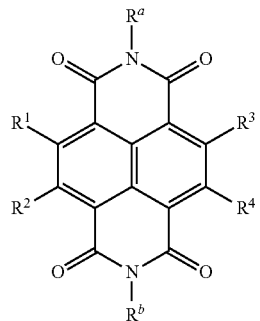

(I.Ba)

in which

R¹ and R⁴ are each Cl and R² and R³ are each hydrogen, or R¹ and R³ are each Cl and R² and R⁴ are each hydrogen, and R$^a$ and R$^b$ are each independently 1H,1H-perfluoro-C₂-C₃₀-alkyl or 1H,1H,2H,2H-perfluoro-C₂-C₃₀-alkyl.

The invention further provides processes for preparing compounds of the general formula (I).

The invention further relates to the use of compounds of the formula (I) as emitter materials, charge transport materials or exciton transport materials.

The invention also provides organic field-effect transistors (OFETs), substrates comprising a multitude of organic field-effect transistors, semiconductor units, organic light-emitting diodes (OLEDs) and organic solar cells, which comprise at least one compound of the formula (I).

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

Figure 1A:
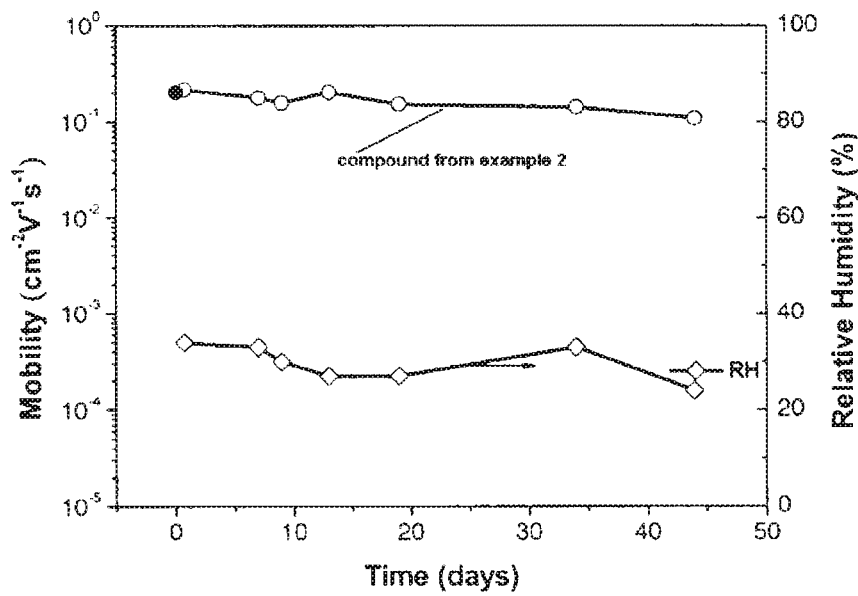
FIG. 1a is a graph of the mobility of compound 2 in air depending on the relative humidity.

In a preferred embodiment, the compounds of the formula (I) are selected from compounds of the formula (I.A)

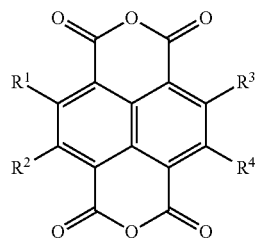

(I.A)

in which R¹, R², R³ and R⁴ are each as defined above and in detail below.

In a further preferred embodiment, the compounds of the formula (I) are selected from compounds of the formulae (I.B)

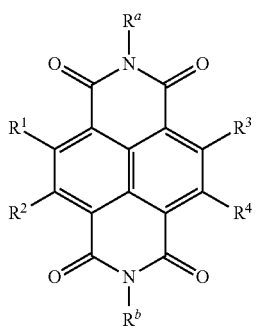

(I.B)

in which at least two of the $R^1$, $R^2$, $R^3$ and $R^4$ radicals are Cl and the remaining radicals are hydrogen; and $R^a$ and $R^b$ are each independently hydrogen or unsubstituted or substituted alkyl, alkenyl, alkadienyl, alkynyl, cycloalkyl, bicycloalkyl, cycloalkenyl, heterocycloalkyl, aryl or heteroaryl.

Preferably, in the compounds of the formula (I.B), $R^a$ and $R^b$ are each independently 1H,1H-perfluoro-$C_2$-$C_{30}$-alkyl, 1H,1H,2H,2H-perfluoro-$C_3$-$C_{30}$-alkyl or branched $C_3$-$C_{30}$-alkyl.

Preferably, in the compounds of the formula (I) and of the formulae (I.A) and (I.B), the $R^1$ and $R^3$ radicals are each chlorine and the $R^2$ and $R^4$ radicals are each hydrogen.

Additionally preferably, in the compounds of the formula (I) and of the formulae (I.A) and (I.B), the $R^1$ and $R^4$ radicals are each chlorine and the $R^2$ and $R^3$ radicals are each hydrogen.

Additionally preferably, in the compounds of the formula (I) and of the formulae (I.A) and (I.B), the $R^1$, $R^2$ and $R^3$ radicals are each chlorine and the $R^4$ radicals are each hydrogen.

Additionally preferably, in the compounds of the formula (I) and of the formulae (I.A) and (I.B), the $R^1$, $R^2$, $R^3$ and $R^4$ radicals are each chlorine.

As used herein, the expression "unsubstituted or substituted alkyl, alkenyl, alkadienyl, alkynyl, cycloalkyl, bicycloalkyl, cycloalkenyl, heterocycloalkyl, aryl or heteroaryl" refers to unsubstituted or substituted alkyl, unsubstituted or substituted alkenyl, unsubstituted or substituted alkadienyl, unsubstituted or substituted alkynyl, unsubstituted or substituted cycloalkyl, unsubstituted or substituted bicycloalkyl, unsubstituted or substituted cycloalkenyl, unsubstituted or substituted heterocycloalkyl, unsubstituted or substituted aryl or unsubstituted or substituted heteroaryl.

In the context of the present invention, the expression "alkyl" comprises straight-chain or branched alkyl. It is preferably straight-chain or branched $C_1$-$C_{70}$-alkyl, especially $C_1$-$C_{30}$-alkyl, more especially $C_1$-$C_{20}$-alkyl, e.g. $C_1$-$C_{12}$-alkyl. Examples of alkyl groups are especially methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl. Preferred branched alkyl groups are swallowtail alkyl groups (see below).

The expression "alkyl" also comprises alkyl radicals whose carbon chains may be interrupted by one or more nonadjacent groups which are selected from —O—, —S—, —$NR^e$—, —C(=O)—, —S(=O)— and/or —S(=O)$_2$—. $R^e$ is preferably hydrogen, alkyl, cycloalkyl, heterocycloalkyl, aryl or hetaryl. The expression alkyl also comprises substituted alkyl radicals. Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, hetaryl, halogen, hydroxyl, mercapto, COOH, carboxylate, $SO_3H$, sulfonate, $NE^1E^2$, nitro and cyano, where $E^1$ and $E^2$ are each independently hydrogen, alkyl, cycloalkyl, heterocycloalkyl, aryl or hetaryl. Halogen substituents are preferably fluorine, chlorine or bromine.

Carboxylate and sulfonate are, respectively, a derivative of a carboxylic acid function or a sulfonic acid function, especially a metal carboxylate or sulfonate, a carboxylic ester or sulfonic ester function or a carboxamide or sulfonamide function. Cycloalkyl, heterocycloalkyl, aryl and hetaryl substituents of the alkyl groups may in turn be unsubstituted or substituted; suitable substituents are those specified below for these groups.

The above remarks regarding alkyl also apply to the alkyl moieties in alkoxy, alkylamino, alkylthio, alkylsulfinyl, alkylsulfonyl, etc.

Aryl-substituted alkyl radicals ("arylalkyl") have at least one unsubstituted or substituted aryl group as defined below. The alkyl group in "arylalkyl" may bear at least one further substituent and/or be interrupted by one or more nonadjacent groups which are selected from —O—, —S—, —$NR^e$—, —CO— and/or —$SO_2$—. $R^e$ has one of the meanings given above. Arylalkyl is preferably phenyl-$C_1$-$C_{10}$-alkyl, more preferably phenyl-$C_1$-$C_4$-alkyl, for example benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl, 4-phenbut-2-yl, 1-(phenmeth)eth-1-yl, 1-(phenmethyl)-1-(methyl)eth-1-yl or (phenmethyl)-1-(methyl)prop-1-yl; preferably benzyl and 2-phenethyl.

In the context of the present invention, the expression "alkenyl" comprises straight-chain and branched alkenyl groups which, depending on the chain length, may bear one or more noncumulated carbon-carbon double bonds (e.g. 1, 2, 3, 4 or more than 4). Alkenyl which has two double bonds is also referred to hereinafter as alkadienyl. Preference is given to $C_2$-$C_{18}$-, particular preference to $C_2$-$C_{12}$-alkenyl groups. The expression "alkenyl" also comprises substituted alkenyl groups which may bear one or more (e.g. 1, 2, 3, 4, 5 or more than 5) substituents. Suitable substituents are, for example, selected from cycloalkyl, heterocycloalkyl, aryl, hetaryl, halogen, hydroxyl, alkoxy, alkylthio, mercapto, COOH, carboxylate, $SO_3H$, sulfonate, $NE^3E^4$, nitro and cyano, where $E^3$ and $E^4$ are each independently hydrogen, alkyl, cycloalkyl, heterocycloalkyl, aryl or hetaryl.

Alkenyl is then, for example, ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-dien-4-yl, hepta-1,4-dien-1-yl, hepta-1,4-dien-3-yl, hepta-1,4-dien-6-yl, hepta-1,4-dien-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl, deca-1,4-dienyl, deca-1,5-dienyl, deca-1,6-dienyl, deca-1,7-dienyl, deca-1,8-dienyl, deca-2,5-dienyl, deca-2,6- dienyl, deca-2,7-dienyl, deca-2,8-dienyl and the like. The remarks regarding alkenyl also apply to the alkenyl groups in alkenyloxy, alkenylthio, etc.

The expression "alkynyl" comprises unsubstituted or substituted alkynyl groups which have one or more nonadjacent triple bonds, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like. The remarks regarding alkynyl also apply to the alkynyl groups in alkynyloxy, alkynylthio, etc. Substituted alkynyls preferably bear one or more (e.g. 1, 2, 3, 4, 5 or more than 5) of the substituents specified above for alkenyl.

In the context of the present invention, the expression "cycloalkyl" comprises unsubstituted or else substituted cycloalkyl groups, preferably $C_3$-$C_5$-cycloalkyl groups such as cyclopropyl, cyclobutyl, cyclopentyl, cyclohexyl, cycloheptyl or cyclooctyl, especially $C_5$-$C_8$-cycloalkyl. Substituted cycloalkyl groups may have one or more (e.g. 1, 2, 3, 4, 5 or more than 5) substituents. These are preferably each independently selected from alkyl, alkoxy, alkylthio and the substituents specified above for the alkyl groups. In the case of substitution, the cycloalkyl groups preferably bear one or more, for example one, two, three, four or five, $C_1$-$C_6$-alkyl groups.

Examples of preferred cycloalkyl groups are cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec-butylcyclohexyl, 2-, 3- and 4-tert-butylcyclohexyl, cycloheptyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, cyclooctyl, 2-, 3-, 4- and 5-methylcyclooctyl, 2-, 3-, 4- and 5-ethylcyclooctyl, 2-, 3-, 4- and 5-propylcyclooctyl.

The expression cycloalkenyl comprises unsubstituted and substituted monounsaturated hydrocarbon groups having from 3 to 8, preferably from 5 to 6 carbon ring members, such as cyclopenten-1-yl, cyclopenten-3-yl, cyclohexen-1-yl, cyclohexen-3-yl, cyclohexen-4-yl and the like. Suitable substituents are those specified above for cycloalkyl.

The expression bicycloalkyl preferably comprises bicyclic hydrocarbon radicals having from 5 to 10 carbon atoms, such as bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl, bicyclo[3.3.0]octyl, bicyclo[4.4.0]decyl and the like. The expression "bicycloalkyl" comprises unsubstituted or else substituted bicycloalkyl groups. Substituted bicycloalkyl groups may have one or more (e.g. 1, 2, 3 or more than 3) substituents. These are preferably each independently selected from alkyl, alkoxy, alkylthio, and the substituents specified above for the alkyl groups.

In the context of the present invention, the expression "aryl" comprises mono- or polycyclic aromatic hydrocarbon radicals which may be unsubstituted or substituted. Aryl is preferably unsubstituted or substituted phenyl, naphthyl, indenyl, fluorenyl, anthracenyl, phenanthrenyl, naphthacenyl, chrysenyl, pyrenyl, etc., and more preferably phenyl or naphthyl. Substituted aryls may, depending on the number and size of their ring systems, have one or more (e.g. 1, 2, 3, 4, 5 or more than 5) substituents. They are preferably each independently selected from alkyl, alkoxy, alkylthio, cycloalkyl, heterocycloalkyl, aryl, hetaryl, halogen, hydroxyl, mercapto, COOH, carboxylate, $SO_3H$, sulfonate, $NE^5E^6$, nitro and cyano, where $E^5$ and $E^6$ are each independently hydrogen, alkyl, cycloalkyl, heterocycloalkyl, aryl or hetaryl. Halogen substituents are preferably fluorine, chlorine or bromine. Aryl is more preferably phenyl which, in the case of substitution, may bear generally 1, 2, 3, 4 or 5, preferably 1, 2 or 3 substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-cyanophenyl.

In the context of the present invention, the expression "heterocycloalkyl" comprises nonaromatic, unsaturated or fully saturated, cycloaliphatic groups having generally from 5 to 8 ring atoms, preferably 5 or 6 ring atoms, in which 1, 2 or 3 of the ring carbon atoms are replaced by heteroatoms selected from oxygen, nitrogen, sulfur and an —$NR^e$— group and which is unsubstituted or substituted by one or more, for example 1, 2, 3, 4, 5 or 6 $C_1$-$C_6$-alkyl groups. $R^e$ is as defined above. Examples of such heterocycloaliphatic groups include pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 1,2-oxazolin-5-yl, 1,3-oxazolin-2-yl and dioxanyl.

In the context of the present invention, the expression "heteroaryl" comprises unsubstituted or substituted, heteroaromatic, mono- or polycyclic groups, preferably the pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl groups, where these heterocycloaromatic groups, in the case of substitution, may bear generally 1, 2 or 3 substituents. The substituents are preferably selected from $C_1$-$C_6$-alkyl, $C_1$-$C_6$-alkoxy, hydroxyl, carboxyl, halogen and cyano.

Nitrogen-containing 5- to 7-membered heterocycloalkyl or heteroaryl radicals which optionally comprise further heteroatoms selected from oxygen and sulfur comprise, for example, pyrrolyl, pyrazolyl, imidazolyl, triazolyl, pyrrolidinyl, pyrazolinyl, pyrazolidinyl, imidazolinyl, imidazolidinyl, pyridinyl, pyridazinyl, pyrimidinyl, pyrazinyl, triazinyl, piperidinyl, piperazinyl, oxazolyl, isooxazolyl, thiazolyl, isothiazolyl, indolyl, quinolinyl, isoquinolinyl or quinaldinyl.

Halogen is fluorine, chlorine, bromine or iodine.

In the compounds of the formula (I) or (I.B), the $R^a$ and $R^b$ radicals may be defined identically or differently. In a preferred embodiment, the $R^a$ und $R^b$ radicals have identical definitions.

In a first preferred embodiment, the $R^a$ und $R^b$ radicals are both hydrogen.

Specific examples of $R^a$ und $R^b$ radicals other than hydrogen are:

methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl; 2-methoxyethyl, 2-ethoxyethyl, 2-propoxyethyl, 2-butoxyethyl, 3-methoxypropyl, 3-ethoxypropyl, 3-propoxypropyl, 3-butoxypropyl, 4-methoxybutyl, 4-ethoxybutyl, 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-butylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 3,6-dithiaheptyl, 3,6-dithiaoctyl, 4,8-dithianonyl, 3,7-dithiaoctyl, 3,7-di-thianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethyl-aminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfinylethyl, 2-ethylsulfinylethyl, 2-propylsulfinylethyl, 2-isopropylsulfinylethyl, 2-butylsulfinylethyl, 2- and 3-methylsulfinylpropyl, 2- and 3-ethylsulfinylpropyl, 2- and 3-propylsulfinylpropyl, 2- and 3-butylsulfinylpropyl, 2- and 4-methylsulfinylbutyl, 2- and 4-ethylsulfinylbutyl, 2- and 4-propylsulfinylbutyl and 4-butylsulfinylbutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 3- and 4-hydroxybutyl and 8-hydroxy-4-oxaoctyl;

2-cyanoethyl, 3-cyanopropyl, 3- and 4-cyanobutyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, butoxy, pentoxy and hexoxy;

methylthio, ethylthio, propylthio, butylthio, pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, butylamino, pentylamino, hexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylamino-carbonyl, pentylaminocarbonyl, hexylaminocarbonyl, heptylaminocarbonyl, octylaminocarbonyl, nonylaminocarbonyl, decylaminocarbonyl and phenylamino-carbonyl;

aminosulfonyl, N-dodecylaminosulfonyl, N,N-diphenylaminosulfonyl, and, N-bis(4-chlorophenyl)aminosulfonyl;

methoxycarbonyl, ethoxycarbonyl, propoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;

diphenylphosphino, di-(o-tolyl)phosphino and diphenylphosphinoxido;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-1,2,3,4-tetrahydroisoquinolinyl), 1-, 2-, 3-, 4-, 5-,6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4, 6-tri-sec.butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4, 6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthyl-azo)phenyl, 4-(2-pyriylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimiidylthio.

Preferred fluorinated $R^a$ and $R^b$ radicals are as follows: 2,2,2-trifluoroethyl, 2,2,3,3,3-pentafluoropropyl, 2,2-difluoroethyl, 2,2,3,3,4,4,4-heptafluorobutyl, 1H,1H-perfluoropentyl, 1H,1H-perfluorohexyl, 1H,1H-perfluoroheptyl, 1H,1H-pentadecafluorooctyl, 1H,1H-perfluorononyl, 1H,1H-perfluorodecyl, 3-bromo-3,3-difluoropropyl, 3,3,4,4, 4-pentafluorobutyl, 1H,1H,2H,2H-perfluoropentyl, 1H,1H, 2H,2H-perfluorohexyl, 1H,1H,2H,2H-perfluoroheptyl, 1H,1H,2H,2H-perfluorooctyl, 1H,1H,2H,2H-perfluorononyl, 1H,1H,2H,2H-perfluorodecyl, 3-(perfluorooctyl) propyl, 4,4-difluorobutyl-, 4,4,4-trifluorobutyl, 5,5,6,6,6-pentafluorohexyl, 2,2-difluoropropyl, 2,2,2-trifluoro-1-phenylethylamino, 1-benzyl-2,2,2-trifluoroethyl, 2-bromo-2,2-difluoroethyl, 2,2,2-trifluoro-1-pyridin-2-ylethyl, 2,2,2-trifluoro-1-(4-methoxyphenyl)ethylamino, 2,2,2-trifluoro-1-phenylethyl, 2,2-difluoro-1-phenylethyl, 1-(4-bromophenyl)-2,2,2-trifluoroethyl, 3-bromo-3,3-difluoropropyl, 3,3,3-trifluoropropylamine, 3,3,3-trifluoro-n-propyl, 3-(perfluorooctyl)propyl, pentafluorophenyl, 2,3, 5,6-tetrafluorophenyl, 4-cyano-(2,3,5,6)-tetrafluorophenyl, 4-carboxy-2,3,5,6-tetrafluorophenyl, 2,4-difluorophenyl, 2,4,5-trifluorophenyl, 2,4,6-trifluorophenyl, 2,5-difluorophenyl, 2-fluoro-5-nitrophenyl, 2-fluoro-5-trifluoromethylphenyl, 2-fluoro-5-methylphenyl, 2,6-difluorophenyl, 4-carboxamido-2,3,5,6-tetrafluorophenyl, 2-bromo-4,6-difluorophenyl, 4-bromo-2-fluorophenyl, 2,3-difluorophenyl, 4-chloro-2-fluorophenyl, 2,3,4-trifluorophenyl, 2-fluoro-4-iodophenyl, 4-bromo-2,3,5,6-tetrafluorophenyl, 2,3,6-trifluorophenyl, 2-bromo-3,4,6-trifluorophenyl, 2-bromo-4,5,6-trifluorophenyl, 4-bromo-2, 6-difluorophenyl, 2,3,4,5-tetrafluorophenyl, 2,4-difluoro-6-nitrophenyl, 2-fluoro-4-nitrophenyl, 2-chloro-6-fluorophenyl, 2-fluoro-4-methylphenyl, 3-chloro-2,4-difluorophenyl, 2,4-dibromo-6-fluorophenyl, 3,5-dichloro-2,4-difluorophenyl, 4-cyano-2-fluorophenyl, 2-chloro-4-fluorophenyl, 2-fluoro-3-trifluoromethylphenyl, 2-trifluoromethyl-6-fluorophenyl, 2,3,4,6-tetrafluorophenyl, 3-chloro-2-fluorophenyl, 5-chloro-2-fluorophenyl, 2-bromo-4-chloro-6-fluorophenyl, 2,3-dicyano-4,5,6-trifluorophenyl, 2,4,5-trifluoro-3-carboxyphenyl, 2,3,4-trifluoro-6-carboxyphenyl, 2,3,5-trifluorophenyl, 4-trifluoromethyl-2,3,5,6-tetrafluorophenyl, 2-fluoro-5-carboxyphenyl, 2-chloro-4,6-difluorophenyl, 6-bromo-3-chloro-2,4-difluorophenyl, 2,3,4-trifluoro-6-nitrophenyl, 2,5-difluoro-4-cyanophenyl, 2,5-difluoro-4-trifluoromethylphenyl, 2,3-difluoro-6-nitrophenyl, 4-trifluoromethyl-2,3-difluorophenyl, 2-bromo-4,6-difluorophenyl, 4-bromo-2-fluorophenyl, 2-nitrotetrafluorophenyl, 2,2',3,3',4',5,5',6,6'-nonafluorobiphenyl, 2-nitro-3,5, 6-trifluorophenyl, 2-bromo-6-fluorophenyl, 4-chloro-2-fluoro-6-iodophenyl, 2-fluoro-6-carboxyphenyl, 2,4-difluoro-3-trifluorophenyl, 2-fluoro-4-trifluorophenyl, 2-fluoro-4-carboxyphenyl, 4-bromo-2,5-difluorophenyl, 2,5-dibromo-3,4,6-trifluorophenyl, 2-fluoro-5-methylsulfonylphenyl, 5-bromo-2-fluorophenyl, 2-fluoro-4-hydroxymethylphenyl, 3-fluoro-4-bromomethylphenyl, 2-nitro-4-trifluoromethylphenyl, 4-trifluoromethylphenyl, 2-bromo-4-trifluoromethylphenyl, 2-bromo-6-chloro-4-(trifluoromethyl)phenyl, 2-chloro-4-trifluoromethylphenyl, 3-nitro-4-(trifluoromethyl)phenyl, 2,6-dichloro-4-(trifluoromethyl)phenyl, 4-trifluorophenyl, 2,6-dibromo-4-(trifluoromethyl)phenyl, 4-trifluoromethyl-2,3,5,6-tetrafluorophenyl, 3-fluoro-4-trifluoromethylphenyl, 2,5-difluoro-4-trifluoromethylphenyl, 3,5-difluoro-4-trifluoromethylphenyl, 2,3-difluoro-4-trifluoromethylphenyl, 2,4-bis(trifluoromethyl)phenyl, 3-chloro-4-trifluoromethylphenyl, 2-bromo-4,5-di(trifluoromethyl)phenyl, 5-chloro-2-nitro-4-(trifluoromethyl)phenyl, 2,4,6-tris(trifluoromethyl)phenyl, 3,4-bis(trifluoromethyl)phenyl, 2-fluoro-3-trifluoromethylphenyl, 2-iodo-4-trifluoromethylphenyl, 2-nitro-4,5-bis(trifluoromethyl)phenyl, 2-methyl-4-(trifluoromethyl)phenyl, 3,5-dichloro-4-(trifluoromethyl)phenyl, 2,3,6-trichloro-4-(trifluoromethyl)phenyl, 4-(trifluoromethyl)benzyl, 2-fluoro-4-(trifluoromethyl)benzyl, 3-fluoro-4-(trifluoromethyl)benzyl, 3-chloro-4-(trifluoromethyl)benzyl, 4-fluorophenethyl, 3-(rifluoromethyl)phenethyl, 2-chloro-6-fluorophenethyl, 2,6-dichlorophenethyl, 3-fluorophenethyl, 2-fluorophenethyl, (2-trifluoromethyl)phenethyl, 4-fluorophenethyl, 3-fluorophenethyl, 4-trifluoromethylphenethyl, 2,3-difluorophenethyl, 3,4-difluorophenethyl, 2,4-difluorophenethyl, 2,5-difluorophenethyl, 3,5-difluorophenethyl, 2,6-difluorophenethyl, 4-(4-fluorophenyl)phenethyl, 3,5-di(trifluoromethyl)phenethyl, pentafluorophenethyl, 2,4-di(trifluoromethyl)phenethyl, 2-nitro-4-(trifluoromethyl)phenethyl, (2-fluoro-3-trifluoromethyl)phenethyl, (2-fluoro-5-trifluoromethyl)phenethyl, (3-fluoro-5-trifluoromethyl)phenethyl, (4-fluoro-2-trifluoromethyl)phenethyl, (4-fluoro-3-trifluoromethyl)phenethyl, (2-fluoro-6-trifluoromethyl)phenethyl, (2,3,6-trifluoro)phenethyl, (2,4,5-trifluoro)phenethyl, (2,4, 6-trifluoro)phenethyl, (2,3,4-trifluoro)phenethyl, (3,4,5-trifluoro)phenethyl, (2,3,5-trifluoro)phenethyl, (2-chloro-5-fluoro)phenethyl, (3-fluoro-4-trifluoromethyl)phenethyl, (2-chloro-5-trifluoromethyl)phenethyl, (2-fluoro-3-chloro-5-trifluoromethyl)phenethyl, (2-fluoro-3-chloro)phenethyl, (4-fluoro-3-chloro)phenethyl, (2-fluoro-4-chloro)phenethyl, (2,3-difluoro-4-methyl)phenethyl, 2,6-difluoro-3-chlorophenethyl, (2,6-difluoro-3-methyl)phenethyl, (2-trifluoromethyl-5-chloro)phenethyl, (6-chloro-2-fluoro-5-methyl)phenethyl, (2,4-dichloro-5-fluoro)phenethyl, 5-chloro-2-fluorophenethyl, (2,5-difluoro-6-chloro)phenethyl, (2,3,4,5-tetrafluoro)phenethyl, (2-fluoro-4-trifluoromethyl)phenethyl, 2,3-(difluoro-4-trifluoromethyl)phenethyl, (2,5-di(trifluoromethyl))phenethyl, 2-fluoro-3,5-dibromophenethyl, (3-fluoro-4-nitro)phenethyl, (2-bromo-4-trifluoromethyl)phenethyl, 2-(bromo-5-fluoro)phenethyl, (2,6-difluoro-4-bromo)phenethyl, (2,6-difluoro-4-chloro)phenethyl, (3-chloro-5-fluoro)phenethyl, (2-bromo-5-trifluoromethyl)phenethyl and the like.

In a very preferred embodiment, the $R^a$ and $R^b$ radicals are each independently 1H,1H-perfluoro-$C_2$-$C_{30}$-alkyl or 1H,1H,2H,2H-perfluoro-$C_3$-$C_{30}$-alkyl, preferably 1H,1H-perfluoro-$C_2$-$C_{20}$-alkyl or 1H,1H,2H,2H-perfluoro-$C_3$-$C_{20}$-alkyl, in particular 1H,1H-perfluoro-$C_2$-$C_{10}$-alkyl or 1H,1H,2H,2H-perfluoro-$C_3$-$C_{30}$-alkyl such as 2,2,2-trifluoroethyl, 2,2,3,3,3-pentafluoropropyl, 2,2,3,3,4,4,4-heptafluorobutyl, 1H,1H-perfluoropentyl, 1H,1H-perfluorohexyl, 1H,1H-perfluoroheptyl, 1H,1H-pentadecafluorooctyl, 1H,1H-perfluorononyl, 1H,1H-perfluorodecyl, 3,3,3-trifluoropropyl, 3,3,4,4,4-pentafluorobutyl, 1H,1H,2H,2H-perfluoropentyl, 1H,1H,2H,2H-perfluorohexyl, 1H,1H,2H,2H-perfluoroheptyl, 1H,1H,2H,2H-perfluorooctyl, 1H,1H,2H,2H-perfluorononyl.

In a further preferred embodiment, the $R^a$ and $R^b$ radicals are selected from groups of the general formula (II)

in which
# represents the bonding site to the imide nitrogen atom,
p is 0 or 1,
x is 2 or 3,
A where present is a $C_1$-$C_{10}$-alkylene group which may be interrupted by one or more nonadjacent groups selected from —O— and —S—,
where, in the case that x is 2, the carbon atom which bears the $R^f$ radicals additionally bears a hydrogen atom,
the $R^f$ radicals are each independently selected from $C_1$-$C_{30}$-alkyl, e.g. $C_4$-$C_{30}$-alkyl which may be interrupted by one or more nonadjacent oxygen atom(s), where at least one of the $R^f$ radicals may also be $C_4$-$C_{30}$-alkyloxy or $C_4$-$C_{30}$-alkylthio.

A preferred radical of the formula (II) is, for example, 2-ethylhex-1-yl.

The $R^a$ and $R^b$ radicals are more preferably selected from groups of the formula (II.1) (so-called swallowtail radicals). Preferably, in the groups of the formula (II.1), the $R^f$ radicals are selected from $C_1$-$C_{30}$-alkyl, preferably $C_1$-$C_{12}$-alkyl, more preferably $C_1$-$C_8$-alkyl, e.g. $C_4$-$C_8$-alkyl, preferably $C_5$-$C_7$-alkyl. The $R^a$ and $R^b$ radicals are then preferably both a group of the formula

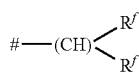

in which
# represents the bonding site to the imide nitrogen atom, and the $R^f$ radicals are independently selected from $C_1$-$C_{30}$-alkyl, preferably $C_1$-$C_{12}$-alkyl, more preferably $C_1$-$C_8$-alkyl. In one embodiment, each $R^f$ radical is independently selected from $C_1$-$C_8$-alkyl, e.g. $C_4$-$C_8$-alkyl, preferably $C_5$-$C_7$-alkyl. The $R^f$ radicals are then specifically linear alkyl radicals which are not interrupted by oxygen atoms. In one embodiment, each $R^f$ has the same meaning. In a further embodiment, each R has a different meaning.

Preferred radicals of the formula II.1 are for example:
1-ethylpropyl, 1-methylpropyl, 1-propylbutyl, 1-ethylbutyl, 1-methylbutyl, 1-butylpentyl, 1-propylpentyl, 1-ethylpentyl, 1-methylpentyl, 1-pentylhexyl, 1-butylhexyl, 1-propylhexyl, 1-ethylhexyl, 1-methylhexyl, 1-hexylheptyl, 1-pentylheptyl, 1-butylheptyl, 1-propylheptyl, 1-ethylheptyl, 1-methylheptyl, 1-heptyloctyl, 1-hexyloctyl, 1-pentyloctyl, 1-butyloctyl, 1-propyloctyl, 1-ethyloctyl, 1-methyloctyl, 1-octylnonyl, 1-heptylnonyl, 1-hexylnonyl, 1-pentylnonyl, 1-butylnonyl, 1-propylnonyl, 1-ethylnonyl, 1-methylnonyl, 1-nonyldecyl, 1-octyldecyl, 1-heptyldecyl, 1-hexyldecyl, 1-pentyldecyl, 1-butyldecyl, 1-propyldecyl, 1-ethyldecyl, 1-methyldecyl, 1-decylundecyl, 1-nonylundecyl, 1-octylundecyl, 1-heptylundecyl, 1-hexylundecyl, 1-pentylundecyl, 1-butylundecyl, 1-propylundecyl, 1-ethylundecyl, 1-methylundecyl, 1-undecyldodecyl, 1-decyldodecyl, 1-nonyldodecyl, 1-octyldodecyl, 1-heptyldodecyl, 1-hexyldodecyl, 1-pentyldodecyl, 1-butyldodecyl, 1-propyldodecyl, 1-ethyldodecyl, 1-methyldodecyl, 1-dodecyltridecyl, 1-undecyltridecyl, 1-decyltridecyl, 1-nonyltridecyl, 1-octyltridecyl, 1-heptyltridecyl, 1-hexyltridecyl, 1-pentyltridecyl, 1-butyltridecyl, 1-propyltridecyl, 1-ethyltridecyl, 1-methyltridecyl, 1-tridecyltetradecyl, 1-undecyltetradecyl, 1-decyltetradecyl, 1-nonyltetradecyl, 1-octyltetradecyl, 1-hetyltetradecyl, 1-hexyltetradecyl, 1-pentyltetradecyl, 1-butyltetradecyl, 1-propyltetradecyl, 1-ethyltetradecyl, 1-methyltetradecyl, 1-pentadecylhexadecyl, 1-tetradecylhexadecyl, 1-tridecylhexadecyl, 1-dodecylhexadecyl, 1-undecylhexadecyl, 1-decylhexadecyl, 1-nonylhexadecyl, 1-octylhexadecyl, 1-heptylhexadecyl, 1-hexylhexadecyl, 1-pentylhexadecyl, 1-butylhexadecyl, 1-propylhexadecyl, 1-ethylhexadecyl, 1-methylhexadecyl, 1-hexadecyloctadecyl, 1-pentadecyloctadecyl, 1-tetradecyloctadecyl, 1-tridecyloctadecyl, 1-dodecyloctadecyl, 1-undecyloctadecyl, 1-decyloctadecyl, 1-nonyloctadecyl, 1-octyloctadecyl, 1-heptyloctadecyl, 1-hexyloctadecyl, 1-pentyloctadecyl, 1-butyloctadecyl, 1-propyloctadecyl, 1-ethyloctadecyl, 1-methyloctadecyl, 1-nonadecyleicosanyl, 1-octadecyleicosanyl, 1-heptadecyleicosanyl, 1-hexadecyleicosanyl, 1-pentadecyleicosanyl, 1-tetradecyleicosanyl, 1-tridecyleicosanyl, 1-dodecyleicosanyl, 1-undecyleicosanyl, 1-decyleicosanyl, 1-nonyleicosanyl, 1-octyleicosanyl, 1-heptyleicosanyl, 1-hexyleicosanyl, 1-pentyleicosanyl, 1-butyleicosanyl, 1-propyleicosanyl, 1-ethyleicosanyl, 1-methyleicosanyl, 1-eicosanyldocosanyl, 1-nonadecyldocosanyl, 1-octadecyldocosanyl, 1-heptadecyldocosanyl, 1-hexadecyldocosanyl, 1-pentadecyldocosanyl, 1-tetradecyldocosanyl, 1-tridecyldocosanyl, 1-undecyldocosanyl, 1-decyldocosanyl, 1-nonyldocosanyl, 1-octyldocosanyl, 1-heptyldocosanyl, 1-hexyldocosanyl, 1-pentyldocosanyl, 1-butyldocosanyl, 1-propyldocosanyl, 1-ethyldocosanyl, 1-methyldocosanyl, 1-tricosanyltetracosanyl, 1-docosanyltetracosanyl, 1-nonadecyltetracosanyl, 1-octadecyltetracosanyl, 1-heptadecyltetracosanyl, 1-hexadecyltetracosanyl, 1-pentadecyltetracosanyl, 1-pentadecyltetracosanyl, 1-tetradecyltetracosanyl, 1-tridecyltetracosanyl, 1-dodecyltetracosanyl, 1-undecyltetracosanyl, 1-decyltetracosanyl, 1-nonyltetracosanyl, 1-octyltetracosanyl, 1-heptyltetracosanyl, 1-hexyltetracosanyl, 1-pentyltetracosanyl, 1-butyltetracosanyl, 1-propyltetracosanyl, 1-ethyltetracosanyl, 1-methyltetracosanyl, 1-heptacosanyloctacosanyl, 1-hexacosanyloctacosanyl, 1-pentacosanyloctacosanyl, 1-tetracosanyloctacosanyl, 1-tricosanyloctacosanyl, 1-docosanyloctacosanyl, 1-nonadecyloctacosanyl, 1-octadecyloctacosanyl, 1-heptadecyloctacosanyl, 1-hexadecyloctacosanyl, 1-hexadecyloctacosanyl, 1-pentadecyloctacosanyl, 1-tetradecyloctacosanyl, 1-tridecyloctacosanyl, 1-dodecyloctacosanyl, 1-undecyloctacosanyl, 1-decyloctacosanyl, 1-nonyloctacosanyl, 1-octyloctacosanyl, 1-heptyloctacosanyl, 1-hexyloctacosanyl, 1-pentyloctacosanyl, 1-butyloctacosanyl, 1-propyloctacosanyl, 1-ethyloctacosanyl, 1-methyloctacosanyl.

More preferred radicals are for example: 1-methylethyl, 1-methylpropyl, 1-methylbutyl, 1-methylpentyl, 1-methylhexyl, 1-methylheptyl, 1-methyloctyl, 1-ethylpropyl, 1-ethylbutyl, 1-ethylpentyl, 1-ethylhexyl, 1-ethylheptyl, 1-ethyloctyl, 1-propylbutyl, 1-propylpentyl, 1-propylhexyl, 1-propylheptyl, 1-propyloctyl, 1-butylpentyl, 1-butylhexyl, 1-butylheptyl, 1-butyloctyl, 1-pentylhexyl, 1-pentylheptyl, 1-pentyloctyl, 1-hexylheptyl, 1-hexyloctyl, 1-heptyloctyl.

Very preferred examples of a group of the formula II.1), wherein each $R^f$ has the same meaning are 1-butylpent-1-yl, 1-pentylhex-1-yl and 1-hexylhept-1-yl. Preferred examples of a group of the formula II.1), wherein each $R^f$ has a different meaning are 2-ethylhexyl, 1-methylbutyl, 1-methylpentyl or 1-methylhexyl.

In a further preferred embodiment, $R^a$ is selected from groups of the formula (III.A): —$(C_nH_{2n})$—
$R^a$ and $R^b$ is selected from groups of the formula (III.B): —$(C_nH_{2n})$—$R^{b1}$, where $R^{a1}$ and $R^{b1}$ are each independently selected from unsubstituted or substituted cycloalkyl, bicycloalkyl, cycloalkenyl, heterocycloalkyl, aryl and hetaryl, and n is an integer from 1 to 4.
$R^a$ is then preferably selected from —$CH_2$—$R^{a1}$, —$CH_2CH_2$—$R^{a1}$, —$CH_2CH_2CH_2$—$R^{a1}$ and —$CH_2CH_2CH_2CH_2$—$R^{a1}$. $R^b$ is then preferably selected from —$CH_2$—$R^{b1}$, —$CH_2CH_2$—$R^{b1}$, —$CH_2CH_2CH_2$—$R^{b1}$ and —$CH_2CH_2CH_2CH_2$—$R^{b1}$.

$R^{a1}$ and $R^{b1}$ are then preferably selected from groups of the general formulae (1) to (16)

(1)

(2)

(3)

(4)

(5)
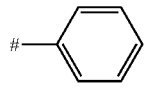

(6)
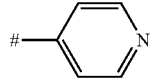

-continued (7)

(8)
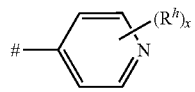

(9)
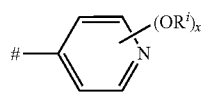

(10)

(10)
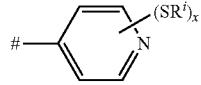

(11)
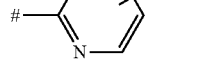

(12)
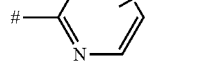

(13)
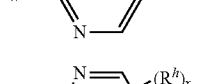

(14)
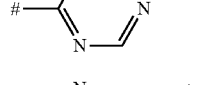

(15)
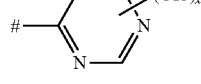

(16)

in which
# represents the bonding site to a $(C_nH_{2n})$ group,
the $R^b$ radicals in the formulae 5, 8, 11 and 14 are each independently selected from $C_1$-$C_3$-alkyl, $C_1$-$C_3$-fluoroalkyl, fluorine, chlorine, bromine, $NE^1E^2$, nitro and cyano, where $E^1$ and $E^2$ are each independently hydrogen, alkyl, cycloalkyl, heterocycloalkyl, aryl or hetaryl,
the $R^i$ radicals in the formulae 6, 7, 9, 10, 12, 13, 15 and 16 are each independently selected from $C_1$-$C_3$-alkyl radicals,
x in the formulae 5, 6 and 7 is 1, 2, 3, 4 or 5,
in the formulae 8, 9 and 10 is 1, 2, 3 or 4,
in the formulae 11, 12 and 13 is 1, 2 or 3,
in the formulae 14, 15 and 16 is 1 or 2.

Preferably, n in the formulae $(C_nH_{2n})$—$R^{a1}$ and $(C_nH_{2n})$—$R^{b1}$ is 1 or 2.

Preferably, $R^a$ and $R^b$ are both

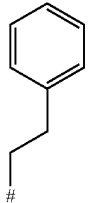

in which # represents the bonding site to an imide nitrogen atom.

In a further preferred embodiment, $R^a$ and $R^b$ are selected from 1,1-dihydroperfluoro-$C_2$-$C_9$-alkyl groups, in particular 1,1-dihydroperfluoro-$C_2$-$C_6$-alkyl groups.

$R^a$ and $R^b$ are then selected from groups of the general formula (IV)

-$CH_2$-(perfluoro-$C_1$-$C_9$-alkyl)   (IV)

in which # represents the bonding site to an imide nitrogen atom, in particular from #-$CH_2$-(perfluoro-$C_1$-$C_5$-alkyl).

Preferred perfluoro-$C_1$-$C_5$-alkyl radicals in the formula (IV) are trifluoromethyl, pentafluoroethyl, n-heptafluoropropyl (n-$C_3F_7$), heptafluoroisopropyl ($CF(CF_3)_2$), n-nonafluorobutyl (n-$C_4F_9$), n-undecafluoropentyl (n-$C_5F_{11}$), and also $C(CF_3)_3$, $CF_2CF(CF_3)_2$, $CF(CF_3)(C_2F_5)$. Preferred perfluoro-$C_6$-$C_9$-alkyl radicals in the formula (IV) include n-$C_6F_{13}$, n-$C_7F_{15}$, n-$C_8F_{17}$ or n-$C_9F_{19}$.

According to a preferred embodiment, $R^a$ and $R^b$ are the same. Preferably, $R^a$ and $R^b$ are both —$CH_2$-(n-$C_3F_7$) or $CH_2$-(n-$C_4F_9$).

In a further preferred embodiment, $R^a$ and $R^b$ are selected from 1,1, 2,2-tetrahydroperfluoro-$C_3$-$C_{10}$-alkyl groups.

$R^a$ and $R^b$ are then selected from groups of the general formula (V)

-$CH_2$—$CH_2$-(perfluoro-$C_1$-$C_8$-alkyl)   (V)

in which # represents the bonding site to an imide nitrogen atom.

Preferred perfluoro-$C_1$-$C_8$-alkyl radicals in the formula (V) are trifluoromethyl, pentafluoroethyl, n-heptafluoropropyl (n-$C_3F_7$), heptafluoroisopropyl ($CF(CF_3)_2$), n-nonafluorobutyl (n-$C_4F_9$), n-undecafluoropentyl (n-$C_5F_{11}$), n-$C_6F_{13}$, n-$C_7F_{13}$, n-$C_8F_{17}$, $C(CF_3)_3$, $CF_2CF(CF_3)_2$, or $CF(CF_3)(C_2F_5)$. According to a preferred embodiment, $R^a$ and $R^b$ are the same.

In a further preferred embodiment, $R^a$ and $R^b$ are each selected from fluorophenylalkyl groups of the general formula (VI)

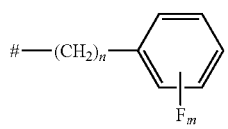   (VI)

in which # represents the bonding site to an imide nitrogen atom,
m is from 1 to 5, and
n is from 1 to 10, preferably from 2 to 5.

In the groups of the general formula (VI), m is preferably 5.

In the compound of the general formula (VI), n is preferably 2.

The fluorophenylalkyl groups of the general formula (VI) are preferably selected from

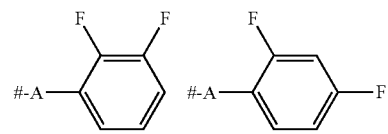

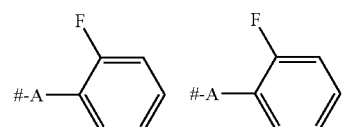

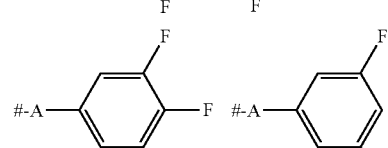

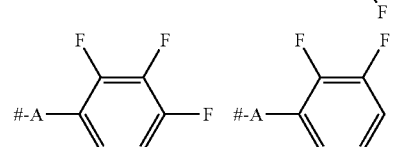

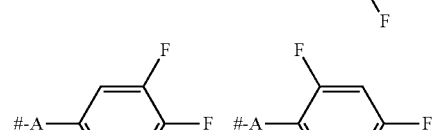

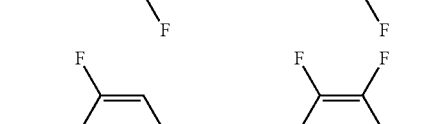

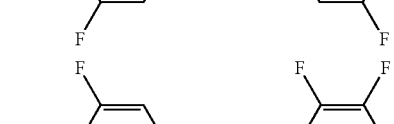

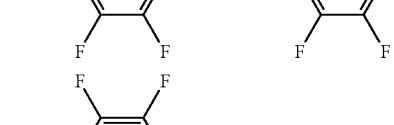

in which # represents the bonding site to an imide nitrogen atom, and
A is $CH_2$, $(CH_2)_2$ or $(CH_2)_3$.

The fluorophenylalkyl groups are more preferably selected from groups of the formulae

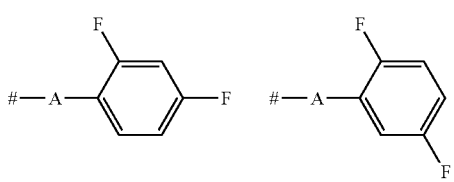

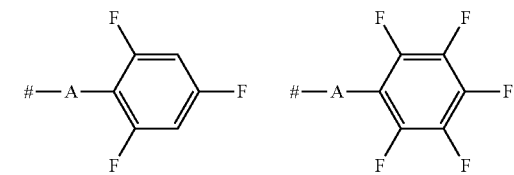

in which # represents the bonding site to an imide nitrogen atom, and
A is $CH_2$, $(CH_2)_2$ or $(CH_2)_3$.

In the formulae shown above, A is especially $(CH_2)_2$.

In a preferred embodiment, $R^a$ and $R^b$ are both

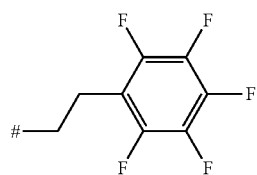

in which # represents the bonding site to an imide nitrogen atom.

In a further preferred embodiment, $R^a$ and $R^b$ are selected from fluorophenyl groups of the general formula (VII)

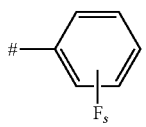

(VII)

in which # represents the bonding site to an imide nitrogen atom, and
s is from 1 to 5.

In a preferred embodiment, $R^a$ and $R^b$ are both

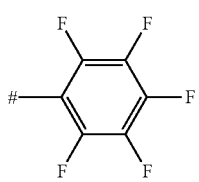

in which # represents the bonding site to an imide nitrogen atom.

A further object of the present invention relates to novel tri- and tetrachlorinated naphthalene compounds of the formula (I), except of 2,3,6,7-tetrachloronaphthalene-1,4,5,8-tetracarboxylic dianhydride and 2,3,6,7-tetrachloronaphthalene-1,4,5,8-tetracarboxylic dimid. Specific examples include those compounds of the formula I, wherein $Z^1$, $Z^2$, $Z^3$, $Z^4$ are each O; $Y^1$ is $NR^a$ with $R^a$ being 1H,1H-perfluoro-$C_2$-$C_{30}$-alkyl or 1H,1H,2H,2H-perfluoro-$C_3$-$C_{30}$-alkyl; $Y^2$ is $NR^b$ with $R^b$ being 1H,1H-perfluoro-$C_2$-$C_{30}$-alkyl or 1H,1H,2H,2H-perfluoro-$C_3$-$C_{30}$-alkyl; $R^1$, $R^2$ and $R^3$ are each Cl and $R^4$ is hydrogen, or $R^1$, $R^2$, $R^3$ and $R^4$ are each Cl.

A further object of the present invention are dichlorinated naphthalenetetracarboxylic diimide compounds of the formula (I.Ba)

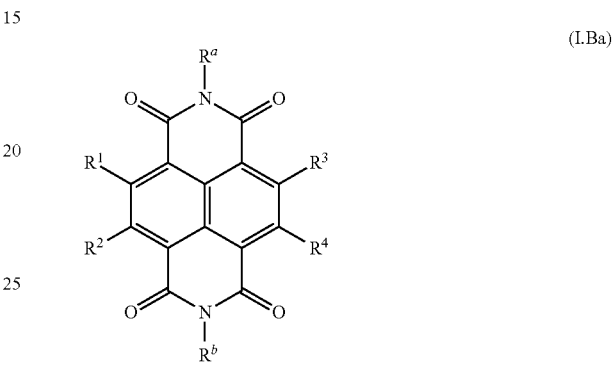

(I.Ba)

wherein $R^a$ and $R^b$ independently are 1H,1H-perfluoro-$C_2$-$C_{30}$-alkyl or 1H,1H,2H,2H-perfluoro-$C_3$-$C_{30}$-alkyl; and $R^1$ and $R^3$ are each Cl and $R^2$ and $R^4$ are each hydrogen or
$R^1$ and $R^3$ are each Cl and $R^2$ and $R^4$ are each hydrogen.

Specific examples of suitable compounds of the formula (I) are shown below.

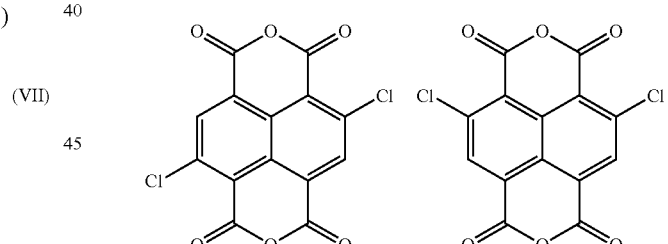

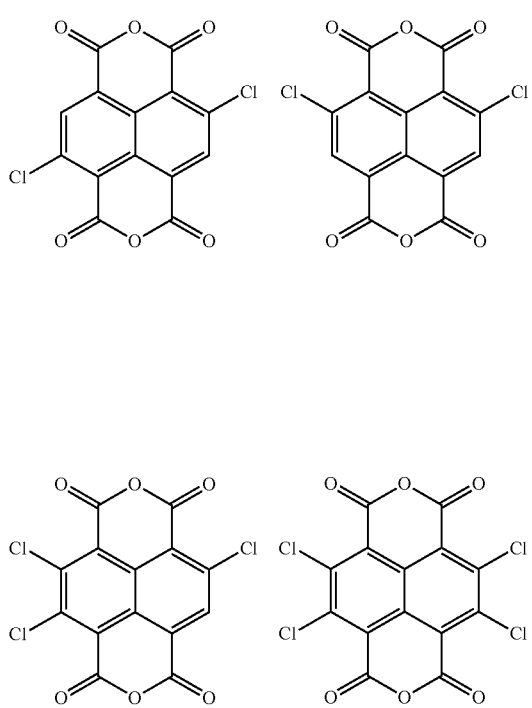

-continued
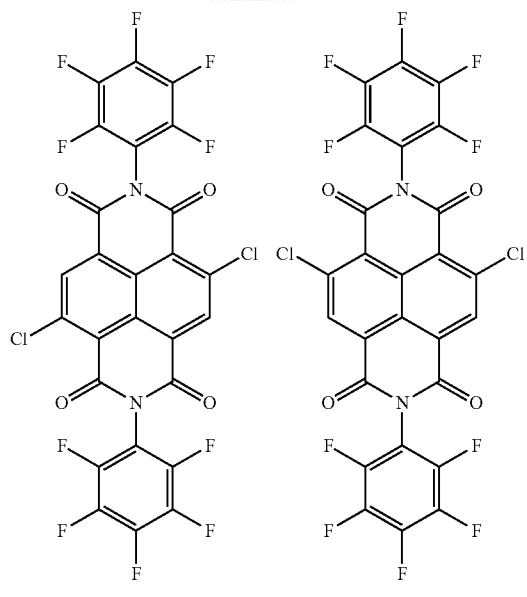
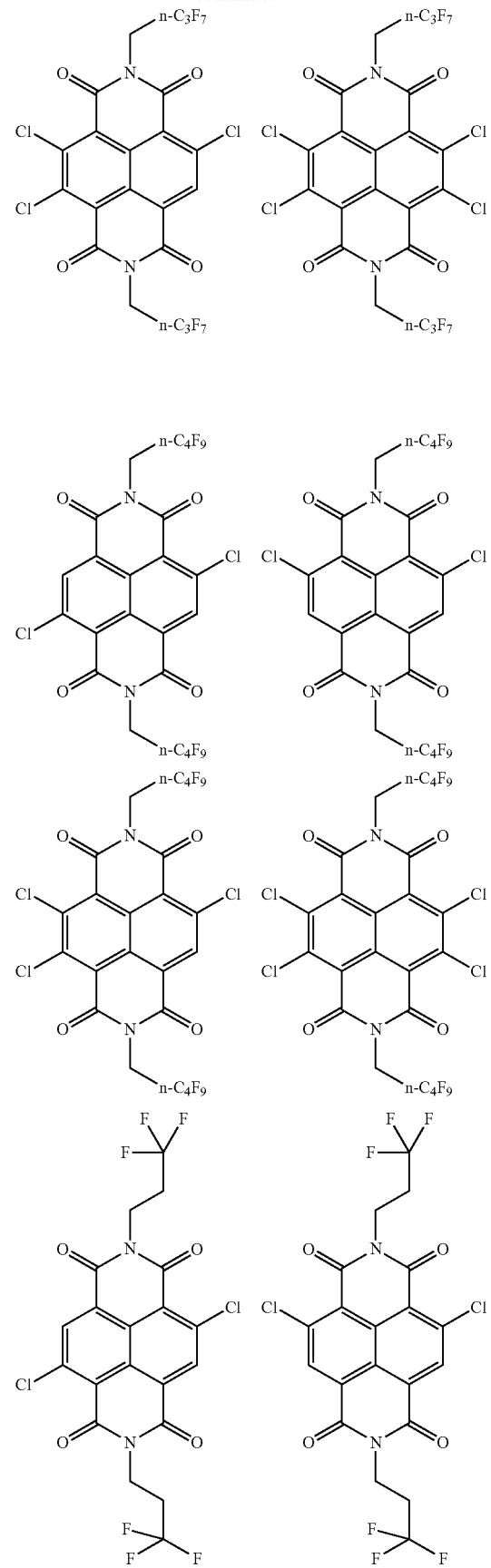

-continued
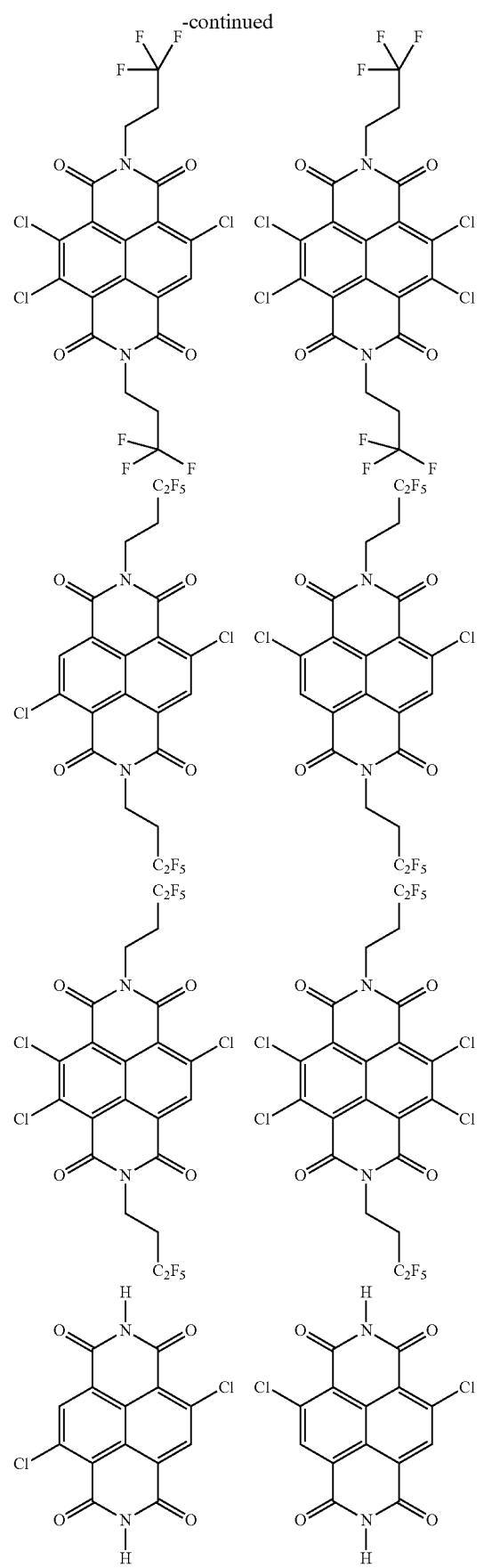
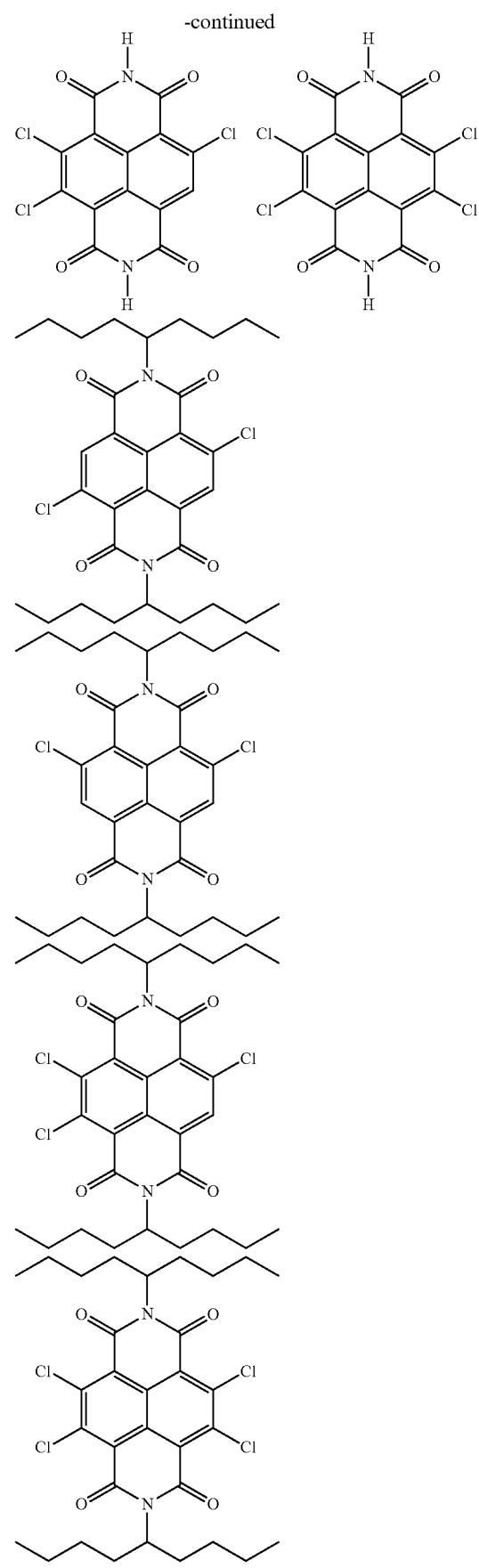

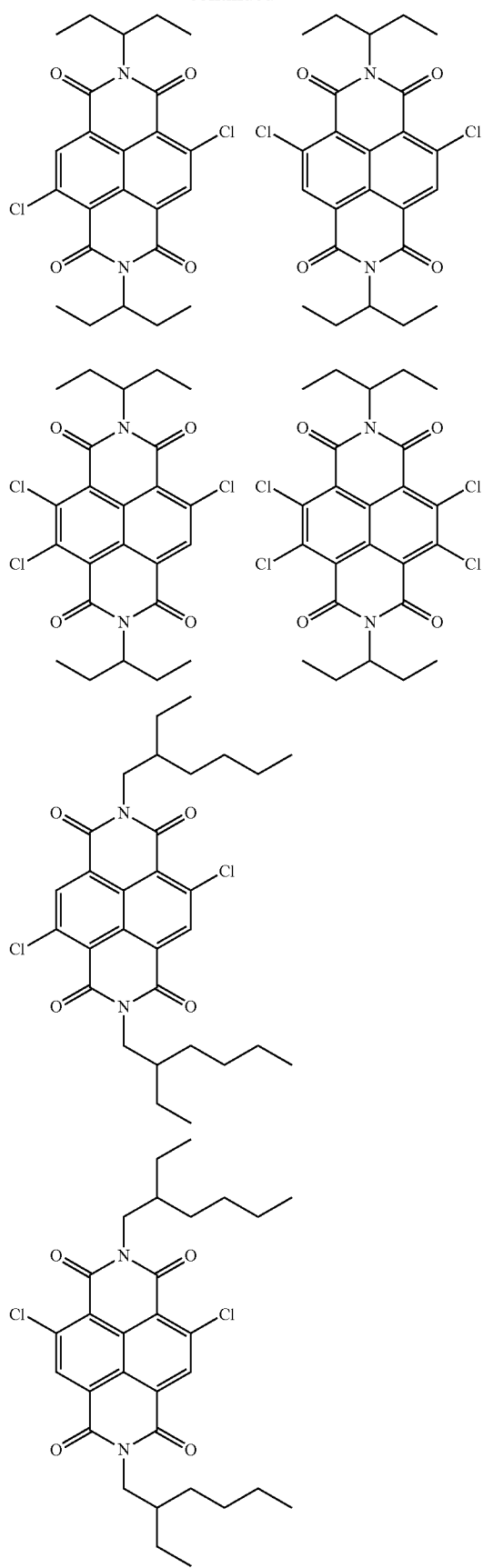
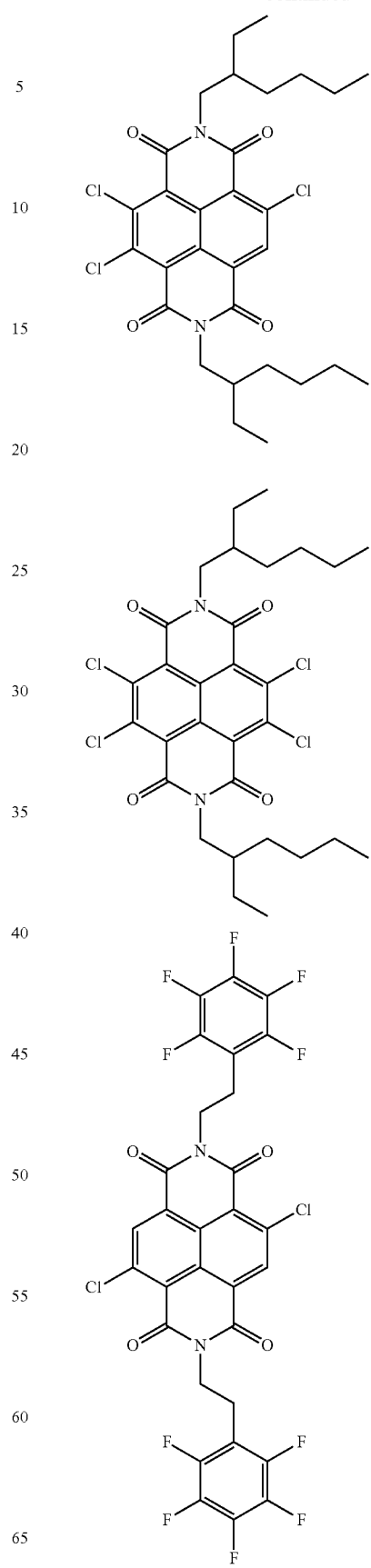

29
-continued
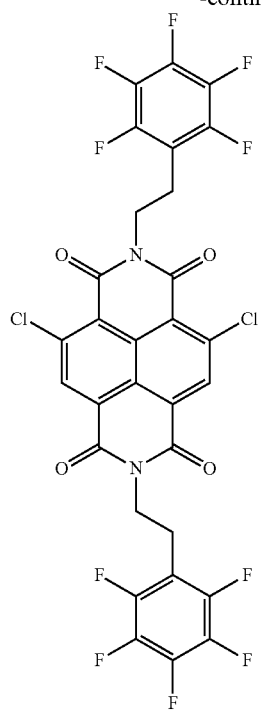
30
-continued
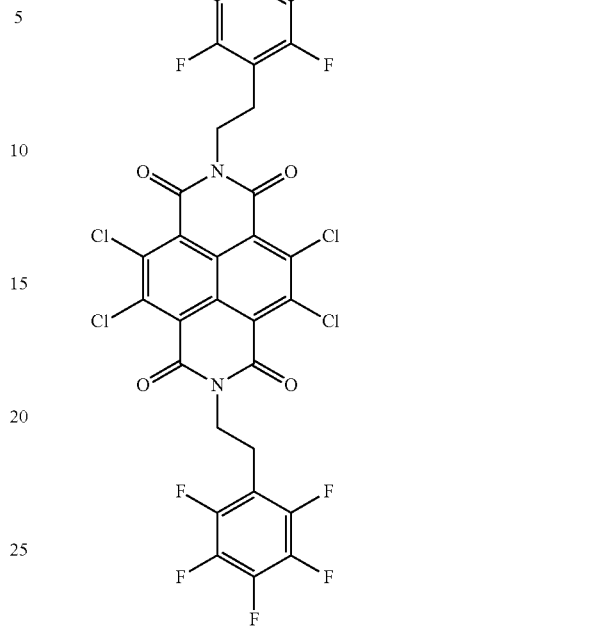
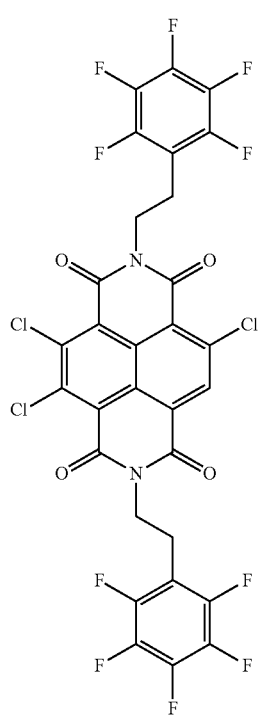

-continued

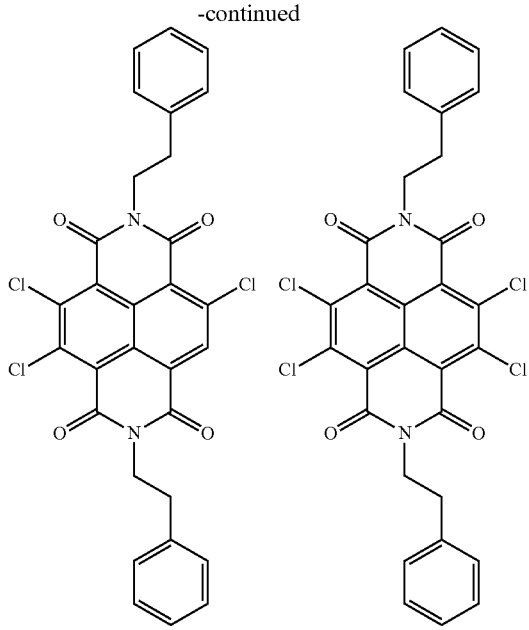

The invention further provides a process for preparing compounds of the formula (I.A)

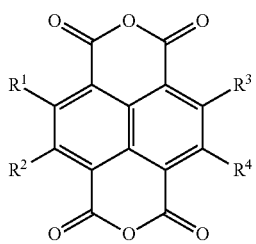
(I.A)

in which
R$^1$, R$^2$ and R$^3$ are each Cl and R$^4$ is hydrogen, or R$^1$, R$^2$, R$^3$ and R$^4$ are each Cl,
in which naphthalene-1,8:4,5-tetracarboxylic dianhydride is subjected to a chlorination by reaction with chlorine in chlorosulfonic acid and if appropriate in the presence of iodine as a catalyst.

Naphthalene-1,8:4,5-tetracarboxylic dianhydride can be chlorinated by reaction with chlorine in chlorosulfonic acid as a solvent.

The reaction of the naphthalene-1,8:4,5-tetracarboxylic dianhydride with a chlorinating agent preferably takes place in the presence of iodine as a catalyst.

The temperature and the duration of the chlorination can be used to control the degree of chlorination of the compounds (I.A).

The reaction temperature for the reaction with a chlorinating agent is typically within a range from 35 to 150° C., preferably 35 to 110° C., more preferably from 60 to 100° C., e.g. from 40 to 95° C.

The reaction of the naphthalene-1,8:4,5-tetracarboxylic dianhydride with a chlorinating agent can be brought about under standard pressure or under elevated pressure, e. g. the chlorination pressure is in the range from 1 bar to 100 bar. Usually the chlorination pressure is in the range from 1 to 10 bar.

The compounds of the formula (I.A) are isolated from the reaction mixture typically by precipitation. The precipitation is brought about, for example, by adding a liquid which does not dissolve the compounds or does so only to a minor degree, but is miscible with the inert solvents. A preferred precipitant is water. The precipitation products can then be isolated by filtration and typically have a sufficiently high purity.

2,3,6,7-Tetrachloronaphthalene-1,4,5,8-tetracarboxylic dianhydride can also be prepared according to the method described in DE 36 20 332.

For use of the products as semiconductors, it may be advantageous to subject the compounds of the formula (I.A) to a further purification. Examples include column chromatography methods, in which case the products, dissolved, for example, in a halogenated hydrocarbon such as methylene chloride or a toluene/- or petroleum ether/ethyl acetate mixture, are subjected to a separation or filtration on silica gel. In addition, purification by sublimation or crystallization is possible.

If required, the purification steps are repeated once or more than once and/or different purification steps are combined in order to obtain very pure compounds (I.A).

The invention further provides a process for preparing compounds of the formulae (I.B)

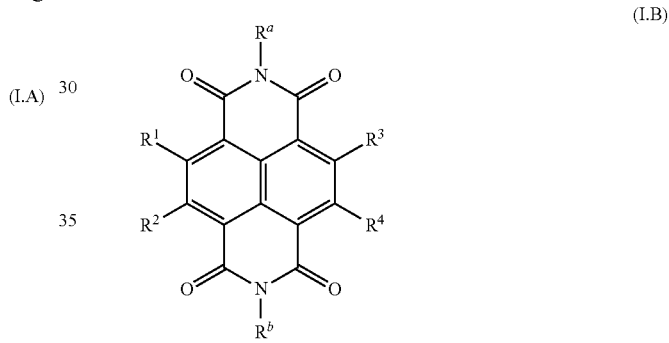
(I.B)

in which
R$^1$, R$^2$ and R$^3$ are each Cl and R$^4$ is hydrogen, or R$^1$, R$^2$, R$^3$ and R$^4$ are each Cl,
R$^a$ and R$^b$ are each independently hydrogen or unsubstituted or substituted alkyl, alkenyl, alkadienyl, alkynyl, cycloalkyl, bicycloalkyl, cycloalkenyl, heterocycloalkyl, aryl or heteroaryl,
in which
a1) naphthalene-1,8:4,5-tetracarboxylic dianhydride is subjected to a chlorination by reaction with chlorine in chlorosulfonic acid and if appropriate in the presence of iodine as a catalyst to obtain a compound of the general formula I.A

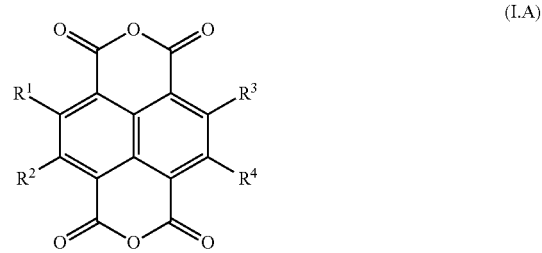
(I.A)

in which

R$^1$, R$^2$ and R$^3$ are each Cl and R$^4$ is hydrogen, or R$^1$, R$^2$, R$^3$ and R$^4$ are each Cl, b1) the compound obtained in step a1) is subjected to a reaction with an amine of the formula R$^a$—NH$_2$ and if appropriate an amine of the formula R$^b$—NH$_2$.

With regard to reaction step a1), reference is made to the above remarks regarding the chlorination of naphthalene-1,8:4,5-tetracarboxylic dianhydride.

The imidation of the carboxylic anhydride groups in reaction steps b1) is known in principle. Preference is given to reacting the anhydride with the primary amine in the presence of a polar aprotic solvent. Suitable polar aprotic solvents are nitrogen heterocycles such as pyridine, pyrimidine, quinoline, isoquinoline, quinaldine, N-methylpiperidine, N-methylpiperidone and N-methylpyrrolidone.

The reaction can be undertaken in the presence of an imidation catalyst. Suitable imidation catalysts are organic and inorganic acids, for example formic acid, acetic acid, propionic acid and phosphoric acid. Suitable imidation catalysts are additionally organic and inorganic salts of transition metals, such as zinc, iron, copper and magnesium. Examples include zinc acetate, zinc propionate, zinc oxide, iron(II) acetate, iron(III) chloride, iron(II) sulfate, copper(II) acetate, copper(II) oxide and magnesium acetate. An imidation catalyst is used preferably in the reaction of aromatic amines and is generally also advantageous for the reaction of cycloaliphatic amines. In the case of reaction of aliphatic amines, especially short-chain aliphatic amines, it is generally possible to dispense with the use of an imidation catalyst. The amount of the imidation catalyst used is generally from 5 to 80% by weight, more preferably from 10 to 75% by weight, based on the total weight of the compound to be amidated.

The quantitative molar ratio of amine to dianhydride is preferably from about 2:1 to 4:1, more preferably from 2.2:1 to 3:1.

The reaction temperature in step b1) is generally from ambient temperature to 200° C., preferably from 40° C. to 180° C. Aliphatic and cycloaliphatic amines are reacted preferably within a temperature range from about 60° C. to 100° C. Aromatic amines are reacted preferably within a temperature range from about 120° C. to 160° C.

The reaction in step b1) is preferably effected under a protective gas atmosphere, for example nitrogen.

The reaction in step b1) can be effected at standard pressure or if desired under elevated pressure. A suitable pressure range is in the range from about 0.8 to 10 bar. When volatile amines are used (boiling point, for instance, ≤180° C.), preference is given to working under elevated pressure.

In general, the diimides obtained in step b1) can be used for the subsequent reactions without further purification. For use of the products as semiconductors, it may, however, be advantageous to subject the products to further purification. Examples include column chromatography methods, in which case the products are preferably dissolved in a halogenated hydrocarbon such as methylene chloride, chloroform or tetrachloroethane and subjected to a separation or filtration on silica gel. Finally, the solvent is removed.

The invention further provides a process for preparing compounds of the formulae (I.B)

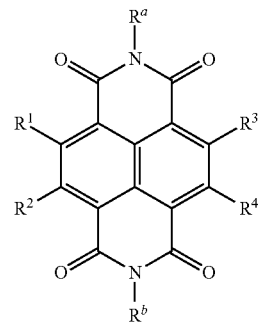

(I.B)

in which

R$^1$ and R$^4$ are each Cl and R$^2$ and R$^3$ are each hydrogen or R$^1$ and R$^3$ are each Cl and R$^2$ and R$^4$ are each hydrogen, or R$^1$, R$^2$ and R$^3$ are each Cl and R$^4$ is hydrogen, or R$^1$, R$^2$, R$^3$ and R$^4$ are each Cl, R$^a$ and R$^b$ are each independently hydrogen or unsubstituted or substituted alkyl, cycloalkyl, bicycloalkyl, heterocycloalkyl, chlorinated aryl or chlorinated hetaryl, in which a2) naphthalene-1,8;4,5-tetracarboxylic dianhydride is subjected to a reaction with an amine of the formula R$^a$—NH$_2$ and if appropriate an amine of the formula R$^b$—NH$_2$ to obtain a compound of the formula (D)

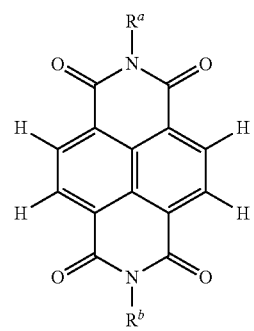

(D)

b2) the compound obtained in step a2) is subjected to a chlorination by reaction with chlorine in the presence of iodine as a catalyst.

In a preferred embodiment, the naphthalene-1,8:4,5-tetracarboxylic dianhydride is converted in step a2) by using amines of the formula R$^a$—NH$_2$ and if appropriate one of the formula R$^b$—NH$_2$, in which R$^a$ and R$^b$ are each groups which cannot be chlorinated by reaction with chlorine in the presence of iodine as a catalyst. Preferably, the chlorination of the compound of the formula (D) in step b2) is brought about by reaction with chlorine in chlorosulfonic acid and in the presence of catalytic amounts of iodine. The amount of iodine is 1 to 10% by weight, preferably 2 to 5% by weight, based on the amount of chlorine.

The reaction temperature for the reaction with chlorine is typically within a range from 40 to 150° C., preferably from 60 to 100° C.

The reaction of the naphthalene-1,8:4,5-tetracarboxylic dianhydride with chlorine can be brought about under standard pressure or under elevated pressure, e. g. the chlorination pressure is in the range from 1 bar to 100 bar. Usually the chlorination pressure is in the range from 1 bar to 10 bar.

The reaction times usually range from 2 to 48 hours, preferably 4 to 16 hours. The reaction temperature and the reaction time of the chlorination can be used to control the degree of chlorination.

Usually, about 50 ml of chlorosulfonic acid are used as solvent for 2 to 20 mmol of compound of formula (D).

Compounds of the formula (I.B) with $R^1$ and $R^4$ are each Cl and $R^2$ and $R^3$ are each hydrogen or $R^1$ and $R^3$ are each Cl and $R^2$ and $R^4$ are each hydrogen may also be prepared as outlined in scheme 1.

Scheme 1:

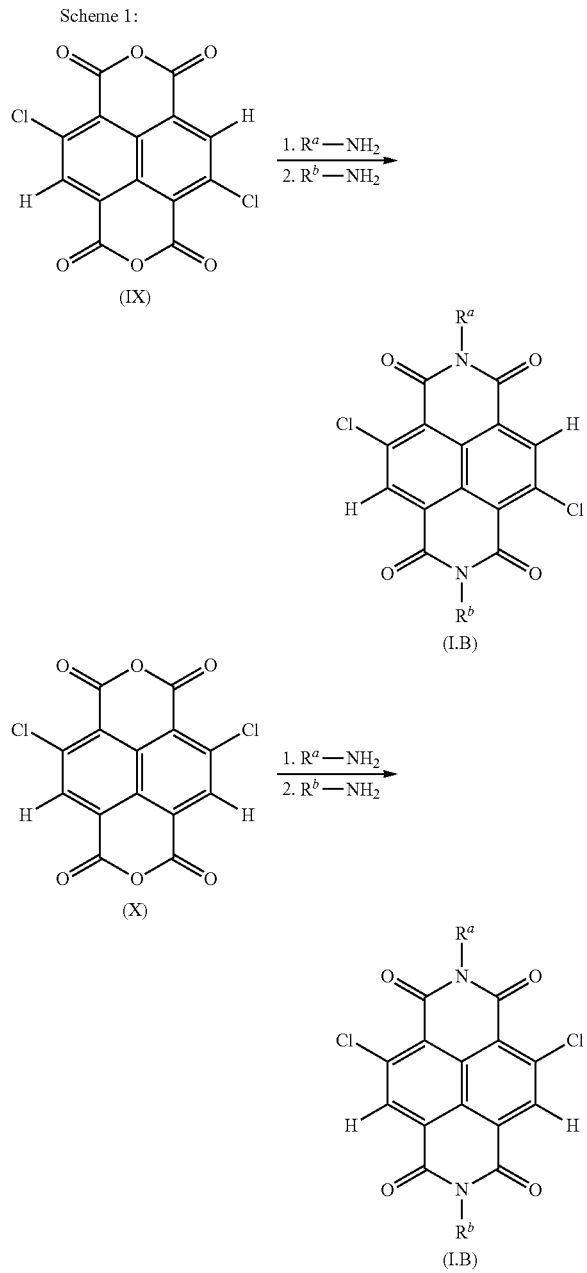

In scheme 1, $R^a$ and $R^b$ are as defined above. The dichloronaphthalenetetracarboxylic bisanhydrides of formulae (IX) and (X), respectively, are treated with an amine of the formula $R^a$—$NH_2$ and if appropriate one of the formula $R^b$—$NH_2$, in the case that $R^a$ is different from $R^b$. The reaction is usually carried out in a solvent. Suitable solvents include $C_1$-$C_6$ alkane carboxylic acids, e.g. acetic acid. 2,6-Dichloronaphthalene-1,4,5,8-tetracarboxylic acid dianhydride of the formula (IX) and 2,7-dichloronaphthalene-1,4,5,8-tetracarboxylic acid dianhydride of the formula (X) (i.e. compounds of the formula (I.A), wherein $R^1$ and $R^4$ are both chlorine and $R^2$ and $R^3$ are both hydrogen or $R^1$ and $R^3$ are both chlorine and $R^2$ and $R^4$ are both hydrogen, respectively) can also be prepared according to the method described in J. Org. Chem. 2006, 71, 8098-8105.

Compounds of the formula (I.B) with $R^1$, $R^2$, $R^3$ and $R^4$ being chlorine can be prepared in analogy to the process depicted in scheme 1 starting from 2,3,6,7-tetrachloronaphthalene-1,4,5,8-tetracarboxylic dianhydride which can be prepared according to the method described in DE 36 20 332.

The compounds of the formula (I) and more specifically of the formulae (I.A) and (I.B) are particularly advantageously suitable as organic semiconductors. They generally function as n-type semiconductors. When the compounds of the formula (I) used in accordance with the invention are combined with other semiconductors and the position of the energy levels has the result that the other semiconductors function as n-type semiconductors, the compounds (I) can also function as p-semiconductors in exceptional cases.

The compounds of the formula (I) are notable for their air stability. Surprisingly, organic field-effect transistors comprising a compound of formula (I) are notable for their air stability and humidity stability.

The compounds of the formula (I) possess a high charge transport mobility and/or have a high on/off ratio. The compounds of the formula (I) have charge mobilities of least 0.1 $cm^2V^{-1}$ $s^{-1}$ when deposited by vacuum-deposition methods or of least 0.01 $cm^2V^{-1}$ $s^{-1}$ when deposited in liquid form. The average on/off ratio is at least $10^4$, preferably at least $10^5$. They are suitable in a particularly advantageous manner for organic field-effect transistors (OFETs).

The inventive compounds are suitable particularly advantageously for the production of integrated circuits (ICs), for which the n-channel MOSFETs (metal oxide semiconductor field-effect transistors (MOSFETs)) customary to date are used. These are then CMOS-like semiconductor units, for example for microprocessors, microcontrollers, static RAM, and other digital logic units.

For the production of semiconductor materials, the inventive compounds of the formula (I) can be processed further by one of the following processes: printing (offset, flexographic, gravure, screen, inkjet, electrophotography), evaporation, laser transfer, spin-coating, photolithography, dropcasting. They are suitable especially for use in displays (especially large-area and/or flexible displays) and RFID tags.

The inventive compounds are also suitable particularly as fluorescence emitters in OLEDs, in which they are excited either by electroluminescence or by an appropriate phosphorescence emitter via Förster energy transfer (FRET).

The inventive compounds of the formula (I) are also particularly suitable in displays which switch colors on and off based on an electrophoretic effect via charged pigment dyes. Such electrophoretic displays are described, for example, in US 2004/0130776.

The invention further provides organic field-effect transistors comprising a substrate having at least one gate structure, a source electrode and a drain electrode and at least one compound of the formula I as defined above as an n-type semiconductor. The invention further provides substrates comprising a multitude of organic field-effect transistors, wherein at least some of the field-effect transistors comprise at least one compound of the formula I as defined above as an n-type semiconductor. The invention also provides semiconductor units which comprise at least one such substrate.

A specific embodiment is a substrate with a pattern (topography) of organic field-effect transistors, each transistor comprising an organic semiconductor disposed on the substrate;
a gate structure for controlling the conductivity of the conductive channel; and
conductive source and drain electrodes at the two ends of the channel, the organic semiconductor consisting of at least one compound of the formula (I) or comprising a compound of the formula (I). In addition, the organic field-effect transistor generally comprises a dielectric.

A further specific embodiment is a substrate having a pattern of organic field-effect transistors, each transistor forming an integrated circuit or being part of an integrated circuit and at least some of the transistors comprising at least one compound of the formula (I).

Suitable substrates are in principle the materials known for this purpose. Suitable substrates comprise, for example, metals (preferably metals of groups 8, 9, 10 or 11 of the Periodic Table, such as Au, Ag, Cu), oxidic materials (such as glass, quartz, ceramics, $SiO_2$), semiconductors (e.g. doped Si, doped Ge), metal alloys (for example based on Au, Ag, Cu, etc.), semiconductor alloys, polymers (e.g. polyvinyl chloride, polyolefins such as polyethylene and polypropylene, polyesters, fluoropolymers, polyamides, polyimides, polyurethanes, polyalkyl (meth)acrylates, polystyrene and mixtures and composites thereof), inorganic solids (e.g. ammonium chloride), paper and combinations thereof. The substrates may be flexible or inflexible, and have a curved or planar geometry, depending on the desired use.

A typical substrate for semiconductor units comprises a matrix (for example a quartz or polymer matrix) and, optionally, a dielectric top layer.

Suitable dielectrics are $SiO_2$, polystyrene, poly-α-methylstyrene, polyolefins (such as polypropylene, polyethylene, polyisobutene), polyvinylcarbazole, fluorinated polymers (e.g. Cytop, CYMM), cyanopullulans, polyvinylphenol, poly-p-xylene, polyvinyl chloride, or polymers crosslinkable thermally or by atmospheric moisture. Specific dielectrics are "self-assembled nanodielectrics", i.e. polymers which are obtained from monomers comprising SiCl functionalities, for example $Cl_1SiOSiCl_3$, $Cl_3Si$—$(CH_2)$—$SiCl_3$, $ClSi$—$(CH_2)_{12}$—$SiCl_3$, and/or which are crosslinked by atmospheric moisture or by addition of water diluted with solvents (see, for example, Faccietti Adv. Mat. 2005, 17, 1705-1725). Instead of water, it is also possible for hydroxyl-containing polymers such as polyvinylphenol or polyvinyl alcohol or copolymers of vinylphenol and styrene to serve as crosslinking components. It is also possible for at least one further polymer to be present during the crosslinking operation, for example polystyrene, which is then also crosslinked (see Facietti, US patent application 2006/0202195).

The substrate may additionally have electrodes, such as gate, drain and source electrodes of OFETs, which are normally localized on the substrate (for example deposited onto or embedded into a nonconductive layer on the dielectric). The substrate may additionally comprise conductive gate electrodes of the OFETs, which are typically arranged below the dielectric top layer (i.e. the gate dielectric).

In a specific embodiment, an insulator layer (gate insulating layer) is present on at least part of the substrate surface. The insulator layer comprises at least one insulator which is preferably selected from inorganic insulators such as $SiO_2$, SiN, etc., ferroelectric insulators such as $Al_2O_3$, $Ta_2O$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 8, 9, 10 or 11 of the Periodic Table, such as Pd, Au, Ag, Cu, Al, Ni, Cr, etc. Also suitable are conductive polymers such as PEDOT (=poly(3,4-ethylenedioxythiophene)); PSS (=poly(styrenesulfonate)), polyaniline, surface-modified gold, etc. Preferred electrically conductive materials have a specific resistance of less than $10^{-3}$ ohm×meter, preferably less than $10^4$ ohm×meter, especially less than $10^{-6}$ or $10^{-7}$ ohm×meter.

In a specific embodiment, drain and source electrodes are present at least partly on the organic semiconductor material. It will be appreciated that the substrate may comprise further components as used customarily in semiconductor materials or ICs, such as insulators, resistors, capacitors, conductor tracks, etc.

The electrodes may be applied by customary processes, such as evaporation, lithographic processes or another structuring process.

The semiconductor materials may also be processed with suitable auxiliaries (polymers, surfactants) in disperse phase by printing.

In a preferred embodiment, the deposition of at least one compound of the general formula I (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of the general formula I are suitable particularly advantageously for use in a PVD process, since they essentially do not decompose and/or form undesired by-products. The material deposited is obtained in high purity. In a specific embodiment, the deposited material is obtained in the form of crystals or comprises a high crystalline content. In general, for the PVD, at least one compound of the general formula (I) is heated to a temperature above its evaporation temperature and deposited on a substrate by cooling below the crystallization temperature. The temperature of the substrate in the deposition is preferably within a range from about 20 to 250° C., more preferably from 50 to 200° C.

The resulting semiconductor layers generally have a thickness which is sufficient for ohmic contact between source and drain electrodes. The deposition can be effected under an inert atmosphere, for example under nitrogen, argon or helium.

The deposition is effected typically at ambient pressure or under reduced pressure. A suitable pressure range is from about $10^{-7}$ to 1.5 bar.

The compound of the formula (I) is preferably deposited on the substrate in a thickness of from to 1000 nm, more preferably from 15 to 250 nm. In a specific embodiment, the compound of the formula I is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic Semi-Conductors", Journal of Crystal Growth 187 (1998), pages 449-454, and in "Physical Vapor Growth of Centimeter-sized Crystals of α-Hexathiophene", Journal of Crystal Growth 1982 (1997), pages 416-427, which are incorporated here by reference.

The compounds of the general formula (I) can also advantageously be processed from solution. In that case, at least one compound of the general formula (I) is applied to a substrate (and if appropriate further semiconductor materials), for example, by spin-coating. In addition, at least one compound of the formula (I) is applied to a substrate by solution shearing. This type of deposition is described e.g. in Adv. Mater. 2008, 20, 2588-2594. This includes the typical knife-coating methods such as airknife-coating, knife-coating, airblade-coating, squeeze-coating, roll-coating and kiss-coating. For this purpose, for example, a solution of the compound of the formula (I) is applied to a first substrate and then a second substrate is brought into contact with the solution. Then shear energy is introduced. According to a preferred embodiment, a small amount of a solution of at least one compound of the formula (I), e.g. a drop, is added on a substrate. The substrate temperatures range between room temperature and a temperature being 60 to 80% of the boiling point of the used solvent to control the solvent evaporation rate. Pulling the top wafer against the stationary wafer exerts a shearing force between wafers on the solution. The shearing speed is usually in the range from 0.01 to 0.5 mm/sec, preferably from 0.0866 to 0.1732 mm/sec. It may be advantageous to use a substrate having a hydrophobic surface. Suitable compounds for hydrophobizing substrate surfaces comprise alkyltrialkoxysilanes, such as n-octadecyltrimethoxysilane, n-octadecyltriethoxysilane, n-octadecyltri(n-propyl)-oxysilane or n-octadecyltri(isopropyl)oxysilane or phenyltrichlorosilane.

In the case, that the compounds of the general formula (I) are processed from solution, the used solvent may have a low boiling point or a high boiling point. Suitable solvents are aromatic solvents such as toluene, xylene, mesitylene, naphthalene, decahydronaphthalene, octahydronaphthalene, chlorobenzene or dichlorobenzene, especially ortho-dichlorobenzene, or linear or cyclic ethers, e.g. tetrahydrofuran, diglycol methyl ether, or aromatic ethers such as diphenylether methoxybenzene, perfluoropolyethers such as HT-60 or HT 90 CT 135 (from Solvay, copolymers of perfluoro-ethyleneglycol, perfluoropropyleneglycol with $CF_3$ radicals at the beginning and the end of the chain), $C_1$-$C_6$-alkylesters of $C_1$-$C_6$-carboxylic acids such as methyl acetate, ethyl acetate, propyl acetate, butyl acetate, methyl propionate, ethyl propionate, propyl propionate, butyl propionate and mixtures thereof. According to a preferred embodiment, a mixture of solvents is used, especially one, wherein the at least two solvents have different boiling points. Preferably the difference in the boiling points is greater than 30° C.

The compounds of the formula (I) are also suitable for producing semiconductor elements, especially OFETs, by a printing process. It is possible for this purpose to use customary printing processes (inkjet, flexographic, offset, gravure; intaglio printing, nanoprinting). Preferred solvents for the use of the compounds of the formula (I) in a printing process are aromatic solvents such as toluene, xylene, cyclic ethers such as dioxane, tetrahydrofuran, or linear ethers such as dimethoxyethane, ethylene glycol diethlyether, tert-butylmethylether etc. It is also possible to add thickening substances such as polymers, for example polystyrene, etc., to these "semiconductor inks". In this case, the dielectrics used are the aforementioned compounds.

In a specific embodiment, the inventive field-effect transistor is a thin-film transistor (TFT). In a customary construction, a thin-film transistor has a gate electrode disposed on the substrate, a gate insulator layer disposed thereon and on the substrate, a semiconductor layer disposed on the gate insulator layer, an ohmic contact layer on the semiconductor layer, and a source electrode and a drain electrode on the ohmic contact layer.

In a preferred embodiment, the surface of the substrate, before the deposition of at least one compound of the general formula (I) (and if appropriate of at least one further semiconductor material), is subjected to a modification. This modification serves to form regions which bind the semiconductor materials and/or regions on which no semiconductor materials can be deposited. The surface of the substrate is preferably modified with at least one compound (C1) which is suitable for binding to the surface of the substrate and to the compounds of the formula (I). In a suitable embodiment, a portion of the surface or the complete surface of the substrate is coated with at least one compound (C1) in order to enable improved deposition of at least one compound of the general formula (I) (and if appropriate further semiconductive compounds). A further embodiment comprises the deposition of a pattern of compounds of the general formula (C1) on the substrate by a corresponding production process. These include the mask processes known for this purpose and so-called "patterning" processes, as described, for example, in US-2007-0190783-A1, which is incorporated here fully by reference.

Suitable compounds of the formula (C1) are capable of a binding interaction both with the substrate and with at least one semiconductor compound of the general formula I. The term "binding interaction" comprises the formation of a chemical bond (covalent bond), ionic bond, coordinative interaction, van der Waals interactions, e.g. dipole-dipole interactions etc., and combinations thereof. Suitable compounds of the general formula (C1) are:

silanes, phosphonic acids, carboxylic acids, hydroxamic acids, such as alkyltrichlorosilanes, e.g. n-octadecyltrichlorosilane; aryltrichlorosilanes, e.g. phenyltrichlorosilane; compounds with trialkoxysilane groups, e.g. alkyltrialkoxysilanes such as n-octadecyltrimethoxysilane, n-octadecyltriethoxysilane, n-octadecyltri(n-propyl)oxysilane, n-octadecyltri(isopropyl)oxysilane; trialkoxyaminoalkylsilanes such as triethoxyaminopropylsilane and N-[(3-triethoxysilyl)propyl]ethylenediamine; trialkoxyalkyl 3-glycidyl ether silanes such as triethoxypropyl 3-glycidyl ether silane; trialkoxyallylsilanes such as allyltrimethoxysilane; trialkoxy(isocyanato-alkyl)silanes; trialkoxysilyl(meth)acryloyloxyalkanes and trialkoxysilyl(meth)-acrylamidoalkanes such as 1-triethoxysilyl-3-acryloyloxypropane.

amines, phosphines and sulfur-comprising compounds, especially thiols.

The compound (C1) is preferably selected from alkyltrialkoxysilanes, especially n-octadecyltrimethoxysilane, n-octadecyltriethoxysilane; phenyltrichlorosiliane; hexaalkyldisilazanes, and especially hexamethyldisilazane (HMDS); $C_8$-$C_{30}$-alkylthiols, especially hexadecanethiol; mercaptocarboxylic acids and mercaptosulfonic acids, especially mercaptoacetic acid, 3-mercaptopropionic acid, mercaptosuccinic acid, 3-mercapto-1-propanesulfonic acid and the alkali metal and ammonium salts thereof.

Various semiconductor architectures comprising the inventive semiconductors are also conceivable, for example top contact, top gate, bottom contact, bottom gate, or else a vertical construction, for example a VOFET (vertical organic field-effect transistor), as described, for example, in US 2004/0046182.

The layer thicknesses are, for example, from 10 nm to 5 µm in semiconductors, from 50 nm to µm in the dielectric; the electrodes may, for example, be from 20 nm to 1 µm thick. The OFETs may also be combined to form other components such as ring oscillators or inverters.

A further aspect of the invention is the provision of electronic components which comprise a plurality of semiconductor components, which may be n- and/or p-semiconductors. Examples of such components are field-effect transistors (FETs), bipolar junction transistors (BJTs), tunnel diodes, converters, light-emitting components, biological and chemical detectors or sensors, temperature-dependent detectors, photodetectors such as polarization-sensitive photodetectors, gates, AND, NAND, NOT, OR, TOR and NOR gates, registers, switches, timer units, static or dynamic stores and other dynamic or sequential, logical or other digital components including programmable circuits.

A specific semiconductor element is an inverter. In digital logic, the inverter is a gate which inverts an input signal. The inverter is also referred to as a NOT gate. Real inverter circuits have an output current which constitutes the opposite of the input current. Typical values are, for example, (0, +5V) for TTL circuits. The performance of a digital inverter reproduces the voltage transfer curve (VTC), i.e. the plot of input current against output current. Ideally, it is a staged function, and the closer the real measured curve approximates to such a stage, the better the inverter is. In a specific embodiment of the invention, the compounds of the formula (I) are used as organic n-type semiconductors in an inverter.

The inventive compounds of the formula (I) and more specifically of the formulae (I.A) and (I.B), are also suitable particularly advantageously for use in organic photovoltaics (OPV).

Organic solar cells generally have a layer structure and generally comprise at least the following layers: anode, photoactive layer and cathode. These layers are generally situated on a substrate customary therefore. The structure of organic solar cells is described, for example, in US 2005/0098726 and US 2005/0224905, which are fully incorporated here by reference.

The invention further provides an organic solar cell comprising at least one compound of the formula I as defined above as a photoactive material.

Suitable substrates for organic solar cells are, for example, oxidic materials (such as glass, ceramic, $SiO_2$, in particular quartz, etc.), polymers (e.g. polyvinyl chloride, polyolefins such as polyethylene and polypropylene, polyesters, fluoropolymers, polyamides, polyurethanes, polyalkyl (meth)acrylates, polystyrene and mixtures and composites thereof) and combinations thereof.

Suitable electrodes (cathode, anode) are in principle metals (preferably of groups 8, 9, 10 or 11 of the Periodic Table, e.g. Pt, Au, Ag, Cu, Al, In, Mg, Ca), semiconductors (e.g. doped Si, doped Ge, indium tin oxide (ITO), gallium indium tin oxide (GITO), zinc indium tin oxide (ZITO), etc.), metal alloys (e.g. based on Pt, Au, Ag, Cu, etc., especially Mg/Ag alloys), semiconductor alloys, etc. One of the electrodes, e.g. the anode used is preferably a material essentially transparent to incident light. This includes, for example, ITO, doped ITO, ZnO, FTO (fluorine doped tin oxide), AZO (aluminum doped ZnO), $TiO_2$, Ag, Au, Pt. The other electrode, e.g. the cathode used is preferably a material which essentially reflects the incident light. This includes, for example, metal films, for example of Al, Ag, Au, In, Mg, Mg/Al, Ca, etc.

The photoactive layer itself comprises at least one, or consists of at least one, layer which has been provided by a process according to the invention and comprises, as an organic semiconductor material, at least one compound of the formula Ia and/or Ib as defined above. In addition to the photoactive layer, there may be one or more further layers. These include, for example, layers with electron-conducting properties (ETLs, electron transport layers)

layers which comprise a hole-conducting material (hole transport layer, HTL) which must not absorb, exciton- and hole-blocking layers (e.g. exciton blocking layers, EBLs) which should not absorb, and multiplication layers.

Suitable exciton- and hole-blocking layers are described, for example, in U.S. Pat. No. 6,451,415.

Suitable materials for exciton blocker layers are, for example, bathocuproin (BCP), 4,4',4"-tris[3-methylphenyl-N-phenylamino]triphenylamine (m-MTDATA) or poly-ethylenedioxythiophene (PEDOT).

The inventive solar cells may be based on photoactive donor-acceptor heterojunctions. Where at least one compound of the formula I is used as an HTM (hole transport material), the corresponding ETM (electron transport material) must be selected such that, after excitation of the compounds, a rapid electron transition to the ETM takes place. Suitable ETMs are, for example, C60 and other fullerenes, perylene-3,4:9,10-bis(dicarboximides) (PTCDI), etc. When at least one compound of the formula I is used as an ETM, the complementary HTM has to be selected such that, after excitation of the compound, a rapid hole transition to the HTM takes place. The heterojunction may have a flat (smooth) design (cf. Two layer organic photovoltaic cell, C. W. Tang, Appl. Phys. Lett., 48 (2), 183-185 (1986) or N. Karl, A. Bauer, J. Holzäpfel, J. Marktanner, M. Möbus, F. Stölzle, Mol. Cryst. Liq. Cryst., 252, 243-258 (1994)). The heterojunction may also be designed as a bulk heterojunction or interpenetrating donor-acceptor network (cf., for example, C. J. Brabec, N. S. Sariciftci, J. C. Hummelen, Adv. Funct. Mater., 11 (1), 15 (2001)).

The compounds of the formula I may be used as a photoactive material in solar cells with MiM, pin, pn, Mip or Min structure (M=metal, p=p-doped organic or inorganic semiconductor, n=n-doped organic or inorganic semiconductor, i=intrinsically conductive system composed of organic layers; cf., for example, B. J. Drechsel et al., Org. Eletron., 5 (4), 175 (2004) or Maennig et al., Appl. Phys. A 79, 1-14 (2004)).

The compounds of the formula I can also be used as photoactive material in tandem cells, as described by P. Peumans, A. Yakimov, S. R Forrest in J. Appl. Phys, 93 (7), 3693-3723 (2003) (cf. U.S. Pat. No. 4,461,922, U.S. Pat. No. 6,198,091 and U.S. Pat. No. 6,198,092).

The compounds of the formula I may also be used as photoactive material in tandem cells composed of two or more stacked MiM, pin, Mip or Min diodes (cf. patent application DE 103 13 232.5) (J. Drechsel et al., Thin Solid Films, 451452, 515-517 (2004)).

The layer thicknesses of the M, n, i and p layers are typically from 10 to 1000 nm, preferably from 10 to 400 nm, more preferably from 10 to 100 nm. Thin layers can be produced by vapor deposition under reduced pressure or in inert gas atmosphere, by laser ablation or by solution- or dispersion-processible processes such as spin-coating, knife-coating, casting processes, spraying, dip-coating or printing (e.g. inkjet, flexographic, offset, gravure; intaglio printing, nanoimprinting).

Suitable organic solar cells may, as mentioned above, comprise at least one inventive compound of the formula I as an electron donor (n-type semiconductor) or electron acceptor (p-semiconductor). In addition to the compounds of the general formula I, the following semiconductor materials are suitable for use in organic photovoltaics:

Phthalocyanines which are unhalogenated or halogenated. These include metal-free phthalocyanines or phthalocyanines comprising divalent metals or groups containing metal atoms, especially those of titanyloxy, vanadyloxy, iron, copper, zinc, etc. Suitable phthalocyanines are especially copper phthalocyanine, zinc phthalocyanine and metal-free phthalocyanine. In a specific embodiment, a halogenated phthalocyanine is used. These include: 2,6,10,14-tetrafluorophthalocyanines, e.g. copper 2,6,10,14-tetrafluorophthalocyanine and zinc 2,6,10,14-tetrafluorophthalocyanine; 1,5,9,13-tetrafluorophthalocyanines, e.g. copper 1,5,9,13-tetrafluorophthalocyanine and zinc 1,5,9,13-tetrafluorophthalocyanine; 2,3,6,7,10,11,14,15-octafluorophthalocyanine, e.g. copper 2,3,6,7,10,11,14,15-octafluorophthalocyanine and zinc 2,3,6,7,10,11,14,15-octafluorophthalocyanine; hexadeeachlorophthalocyanines and hexadecafluorophthalocyanines, such as copper hexadeeachlorophthalocyanine, zinc hexadeeachlorophthalocyanine, metal-free hexadeeachlorophthalocyanine, copper hexadecafluorophthalocyanine, hexadecafluorophthalocyanine or metal-free hexadefluorophthalocyanine.

Porphyrins, for example 5,10,15,20-tetra(3-pyridyl)porphyrin (TpyP), or else tetrabenzoporphyrins, for example metal-free tetrabenzoporphyrin, copper tetrabenzoporphyrin or zinc tetrabenzoporphyrin. Especially preferred are tetrabenzoporphyrins which, like the compounds of the formula (I) used in accordance with the invention, are processed from solution as soluble precursors and are converted to the pigmentary photoactive component by thermolysis on the substrate.

Acenes, such as anthracene, tetracene, pentacene, each of which may be unsubstituted or substituted. Substituted acenes preferably comprise at least one substituent which is selected from electron-donating substituents (e.g. alkyl, alkoxy, ester, carboxylate or thioalkoxy), electron-withdrawing substituents (e.g. halogen, nitro or cyano) and combinations thereof. These include 2,9-dialkylpentacenes and 2,10-dialkylpentacenes, 2,10-dialkoxypentacenes, 1,4,8,11-tetraalkoxypentacenes and rubrene (5,6,11,12-tetraphenylnaphthacene). Suitable substituted pentacenes are described in US 2003/0100779 and U.S. Pat. No. 6,864,396, which are hereby incorporated by reference. A preferred acene is rubrene.

Liquid-crystalline (LC) materials, for example coronenes, such as hexabenzocoronene (HBC-PhC$_{12}$), coronenediimides, or triphenylenes such as 2,3,6,7,10,11-hexahexylthiotriphenylene (HTT$_6$), 2,3,6,7,10,11-hexakis(4-n-nonylphenyl)triphenylene (PTP$_9$) or 2,3,6,7,10,11-hexakis(undecyloxy)triphenylene (HAT$_{11}$). Particular preference is given to liquid-crystalline materials which are discotic.

Thiophenes, oligothiophenes and substituted derivatives thereof; suitable oligothiophenes are quaterthiophenes, quinquethiophenes, sexithiophenes, α,ω-di(C$_1$-C$_8$)-alkyloligothiophenes, such as α,ω-dihexylquaterthiophene, α,ω-dihexylquinquethiophene and α,ω-dihexylsexithiophene, poly(alkylthiophenes), such as poly(3-hexylthiophene), bis(dithienothiophenes), anthradithiophenes and dialkylanthradithiophenes such as dihexylanthradithiophene, phenylene-thiophene (P-T) oligomers and derivatives thereof, especially α,ω-alkyl-substituted phenylene-thiophene oligomers.

Also suitable are compounds of the α,α'-bis(2,2-dicyanovinyl)quinquethiophene (DCV5T) type, 3-(4-octylphenyl)-2,2'-bithiophene (PTOPT) type, poly(3-(4'-(1,4,7-trioxaoctyl)phenyl)thiophene) (PEOPT) type, poly(3-(2'-methoxy-5'-octylphenyl)thiophene) (POMeOPT) type, poly(3-octylthiophene) (P$_3$OT) type, poly(pyridopyrazinevinylene)-polythiophene blends, such as EHH-PpyPz, PTPTB copolymers, BBL copolymers, F$_8$BT copolymers, PFMO copolymers; see Brabec C., Adv. Mater., 2996, 18, 2884, (PCPDTBT) poly[2,6-(4,4-bis(2-ethylhexyl)-4H-cyclopenta[2,1 b;3,4 b']dithiophene)-4,7-(2,1,3-benzothiadiazole).

Paraphenylenevinylene and oligomers or polymers comprising paraphenylenevinylene, for example polyparaphenylenevinylene, MEH-PPV (poly(2-methoxy-5-(2'-ethylhexyloxy)-1,4-phenylenevinylene), MDMO-PPV (poly(2-methoxy-5-(3',7'-dimethyloctyloxy)-1,4-phenylenevinylene)), PPV, CN-PPV (with various alkoxy derivatives).

Phenyleneethynylene/phenylenevinylene hybrid polymers (PPE-PPV).

Polyfluorenes and alternating polyfluorene copolymers, for example with 4,7-dithien-2'-yl-2,1,3-benzothiadiazole; also suitable are poly(9,9'-dioctylfluorene-co-benzothiadiazole) (F$_8$BT), poly(9,9'-dioctylfluorene-co-bis-N,N'-(4-butylphenyl)bis-N,N'-phenyl-1,4-phenylenediamine (PFB).

Polycarbazoles, i.e. oligomers and polymers comprising carbazole.

Polyanilines, i.e. oligomers and polymers comprising aniline.

Triarylamines, polytriarylamines, polycyclopentadienes, polypyrroles, polyfurans, polysiloles, polyphospholes, TPD, CBP, Spiro-MeOTAD.

Fullerenes; in such cells, the fullerene derivative is a hole conductor.

In the context of this application, the term "fullerene" refers to a material which is composed of carbon and has a regular, three-dimensional network of fused carbon rings. These may have spherical, cylindrical, ovoid, flattened or angular structures. Suitable fullerenes are, for example, C60, C70, C76, C80, C82, C84, C86, C90, C96, C120, single-walled carbon nanotubes (SWNT) and multi-walled carbon nanotubes (MWNT). Examples of fullerene derivatives are phenyl-C$_{61}$-butyric acid methyl ester (PCBM), phenyl-C$_{71}$-butyric acid methyl ester ([71]PCBM), phenyl-C$_{84}$-butyric acid methyl ester ([84]PCBM), phenyl-C$_{61}$-butyric acid butyl ester ([60]PCBB), phenyl-C$_{61}$-butyric acid octyl ester ([60]PCBO) and thienyl-C$_{61}$-butyric acid methyl ester([60]ThCBM). Particular preference is given to using C60 or PCBM (=[6,6]-phenyl-C61-butyric acid methyl ester).

Particular preference is given to using, in organic solar cells, a combination of semiconductor materials which comprises at least one inventive compound and a halogenated phthalocyanine.

Rylenes. In this context, the term "rylenes" generally refers to compounds having a molecular moiety composed of peri-linked naphthalene units. According to the number of naphthalene units, they may be perylenes (n=2), terrylenes (n=3), quaterrylenes (n=4) or higher rylenes. Accordingly, they may be perylenes, terrylenes or quaterrylenes of the following formula

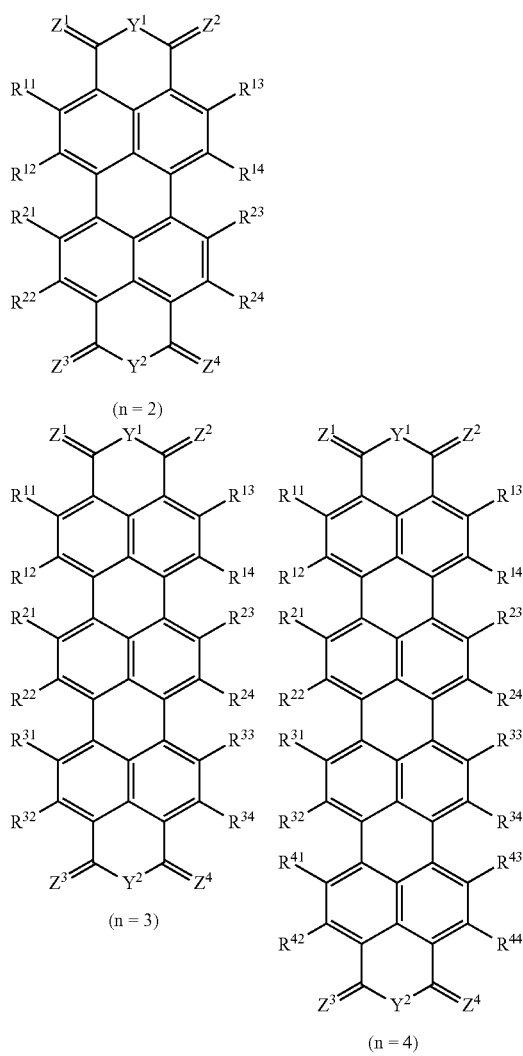

(n = 2)

(n = 3)

(n = 4)

in which
the $R^{n1}$, $R^{n2}$, $R^{n3}$ and $R^{n4}$ radicals, when n=from 1 to 4, may each independently be hydrogen, halogen or groups other than halogen,
$Y^1$ is O or $NR^a$, where $R^a$ is hydrogen or an organyl radical,
$Y^2$ is O or $NR^b$, where $R^b$ is hydrogen or an organyl radical,
$Z^1$, $Z^2$, $Z^3$ and $Z^4$ are each O,
where, in the case that $Y^1$ is $NR^a$, one of the $Z^1$ and $Z^2$ radicals may also be $NR^c$, where the $R^a$ and $R^c$ radicals together are a bridging group having from 2 to 5 atoms between the flanking bonds, and
where, in the case that $Y^2$ is $NR^b$, one of the $Z^3$ and $Z^4$ radicals may also be $NR^d$, where the $R^b$ and $R^d$ radicals together are a bridging group having from 2 to 5 atoms between the flanking bonds.

Suitable rylenes are described, for example, in WO2007/074137, WO2007/093643 and WO2007/116001 (=PCT/EP2007/053330), which are hereby incorporated by reference.

Particular preference is given to using, in organic solar cells, a combination of semiconductor materials which comprises at least one inventive compound of the formula I.

All aforementioned semiconductor materials may also be doped. In a specific embodiment, in the inventive organic solar cells, the compound of the formula I and/or (if present) a further semiconductor material different therefrom is thus used in combination with at least one dopant. Suitable dopants for use of the compounds I as n-type semiconductors are, for example, pyronin B and rhodamine derivatives.

The invention further relates to an organic light-emitting diode (OLED) which comprises at least one compound of the formula I.

Organic light-emitting diodes are in principle formed from a plurality of layers. These include: 1. anode, 2. hole-transporting layer, 3. light-emitting layer, 4. electron-transporting layer and 5. cathode. It is also possible that the organic light-emitting diode does not have all of the layers mentioned; for example, an organic light-emitting diode comprising layers (1) (anode), (3) (light-emitting layer) and (5) (cathode) is likewise suitable, in which case the functions of layers (2) (hole-transporting layer) and (4) (electron-transporting layer) are assumed by the adjacent layers. OLEDs which have layers (1), (2), (3) and (5) or layers (1), (3), (4) and (5) are likewise suitable. The structure of organic light-emitting diodes and processes for their production are known in principle to those skilled in the art, for example from WO 2005/019373. Suitable materials for the individual layers of OLEDs are disclosed, for example, in WO 00/70655. Reference is made here to the disclosure of these documents. Compounds I can be applied to a substrate by deposition from the gas phase by customary techniques, i.e. by thermal evaporation, chemical vapor deposition and other techniques.

The invention is illustrated in detail with reference to the following nonrestrictive examples.

EXAMPLES

I. Preparation of compounds of formula (I.B)

Example 1

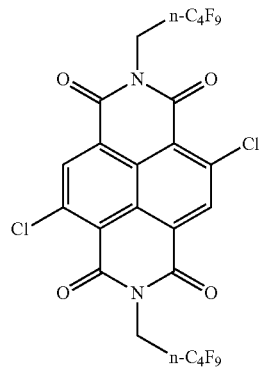

550 mg (1.63 mmol) of isomer-pure 2,6-dichloro-1,4,5,8-naphthalenetetracarboxylic dianhydride (prepared as described in J. Org. Chem. 2006, 71, 8098-8105) are added to 25 ml of acetic acid together with 1.62 g (6.52 mmol) of 1H,1H-perfluoropentylamine and heated to 140° C. for one hour. Thereafter, the acetic acid is removed under reduced pressure and the solids are washed several times with methanol. In order to remove excess reactant, the product is boiled with 2% $NaHCO_3$ solution and the undissolved solids are purified by column chromatography (THF). 420 mg (32%) of a yellowish solid are obtained.

The purification is effected by three-zone gradient sublimation, the zones being at 200° C., 150° C. and 116° C. From a loading of 300 mg, 157 mg of sublimed product are obtained.

The UV-vis spectrum of compound of example 4.3 in ortho-dichlorobenzene showed no absorption in the wavelength range above 450 nm.

The title compound showed a toluene solubility of 1% by weight at room temperature and a tetrahydrofuran solubility of 3% by weight at room temperature.

Example 2

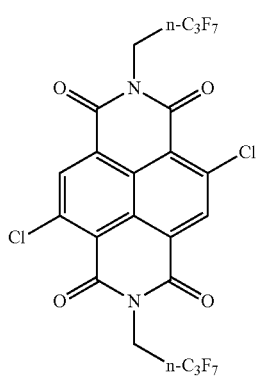

The synthesis was effected as described in example 1, except that 1H,1H-perfluorobutylamine was used. The compound was purified by sublimation using a three zone furnace at 180, 130 and 100° C. Starting from 302 mg of the title compound, 177 mg of purified product were obtained.

The UV-vis spectrum of the compound of example 2 in ortho-dichlorobenzene showed no absorption in the wavelength range above 450 nm.

The title compound showed a toluene solubility of 0.8% by weight at room temperature and a tetrahydrofuran solubility of 1.5% by weight at room temperature.

Example 3

General procedure for preparing bis(1H,1H-perfluoroalkyl)-1,4,5,8-naphtalene tetracarboxylicdiimides of the formula (D) with $R^a$ and $R^b$ being 1H,1H-perfluoroalkyl

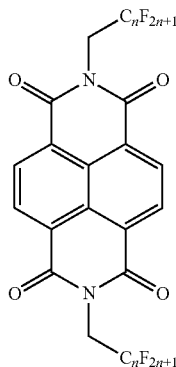

wherein n is 1 to 30

A mixture of 25 ml of N-methylpyrrolidone (NMP), 3 ml of acetic acid, 2.68 g (0.01 mol) of 1,4,5,8-naphthalenetetracarboxylic dianhydride and 0.05 mol 1H,1H-perfluoroalkylamine were heated at 90° C. for 5 hours. Subsequently, the reaction mixture was poured onto 100 ml of diluted hydrochloric acid, filtrated and washed several times with about 50 ml of water and then with ethanol followed by drying at 70° C. under reduced pressure. The crude products may be purified by crystallization from dichloromethane. The title compounds were obtained in a yield of 65 to 90%.

Example 4

General procedure for preparing tetrachlorinated compounds of the formula (I.B) with $R^a$ and $R^b$ being 1H,1H-perfluoroalkyl and $R^1$, $R^2$, $R^3$ and $R^4$ being chlorine

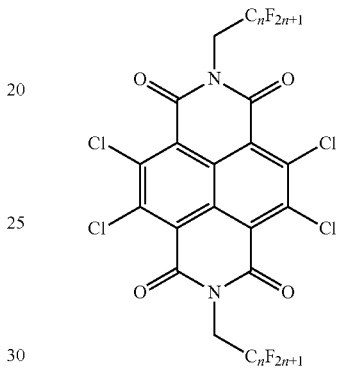

wherein n is 1 to 30.

The product obtained under example 3 (about 3.0 to 5.0 g) in chlorosulfonic acid (50 ml) was admixed with iodine (1.0 g) and heated. At a temperature of 85° C., 1 bar of chlorine was introduced into the reaction mixture over a period of 8 to 16 hours, the chlorine gas being introduced under the surface of the solution. The course of the reaction was monitored by DC. After cooling to room temperature, the reaction mixture is added to water. The solid which precipitates out is filtered off and washed with water and dried under reduced pressure. The yield of the title compound ranges from 62 to 98% with a purity of about 90% (DC). The title compounds were purified by crystallisation from toluene and/or dichloromethane or by column chromatography.

The compounds can be further purified by sublimation using a three zone furnace. For example: compound of example 4.3: sublimation at 200, 140 and 100° C.; compound of example 4.4: sublimation at 230, 160 and 100° C. Starting from 591 mg of compound of example 4.4, 436 mg of sublimated compound were obtained.

The UV-vis spectrum of the compound of example 4.3 in ortho-dichlorobenzene showed no absorption in the wavelength range above 450 nm.

Toluene and tetrahydrofuran (THF) solubilities for title compounds with n=1, 2, 3 and 4 were determined at room temperature.

| Ex. | n | toluene solubility in % by weight | THF solubility in % by weight |
|---|---|---|---|
| 4.1 | 1 | 1 | 4 |
| 4.2 | 2 | 2 | 4 |
| 4.3 | 3 | 2 | 4 |
| 4.4 | 4 | 1.5 | 4 |

II. Performance Results when Used in Field-Effect Transistors:

All performance tests were carried out with compounds purified by gradient sublimation.

II.1 Production of Semiconductor Substrates by Means of Deposition from the Gas Phase Highly doped n-type (100) silicon wafers (conductivity<0.004 $\Omega^{-1}$ cm) were used as substrates for the devices. SiO$_2$ layer (unit area capacitance $C_i$=10 nF/cm$^2$) as gate dielectric were thermally grown to 3000 Å thickness onto the Si substrates. The SiO$_2$/Si substrates were then cleaned with a piranha solution (a 7:3 mixture of H$_2$SO$_4$ and H$_2$O$_2$ by vol %) for 30 min, rinsed with deionized water and dried using a nitrogen gun, the Sio$_2$/Si water were subsequently treated with UV-ozone plasma (Jetlight UVO-cleaner Model 42-100V) for 20 min. Organic semiconductor thin films (45 nm) were vapor-deposited onto the Si/SiO$_2$ substrates held at well-defined temperatures (see table 1) with a deposition rate in the range from 0.2 to 0.3 Å/s and a pressure of $10^{-6}$ torr employing a vacuum deposition chamber (Angstrom Engineering Inc., Canada). Thin film transistors in top-contact configuration were used to measure the charge mobility of the materials. Gold source and drain electrodes (typical channel length were 100 μm with width/length ratios about 20) were vapor-deposited through a shadow mask. The current-voltage (I-V) characteristics of the devices were measured using Keithley 4200-SCS semiconductor parameter analyzer. Key device parameters, such as charge carrier mobility (μ), threshold voltage ($V_T$) and on-to-off current ratio ($I_{on}/I_{off}$) were extracted from the source-drain current ($I_d$) VS. gate voltage ($V_g$) characteristics employing standard procedures. The mobility was determined in the saturation regime from the slope of plots of $(I_{DS})^{1/2}$ versus $V_G$.

Surface Treatment (Optional)

OTS-V

After the cleaning of the SiO$_2$-coated wafer, the SiO$_2$/Si substrates were spin-coated with a 3 mM solution of octadecyltrimethoxysilane (OTS) in trichloroethylene, then placed in an environment saturated with ammonia vapor for 12 h, followed by sonication cleaning, sequential washing and drying. Finally, the organic semiconductor was vacuum-deposited as described above.

TABLE 1

Field field-effect mobilities (μ), on/off ratios (Ion/Ioff), and threshold voltages (Vt) for compounds of formula (I.B) at various substrate temperatures ($T_{sub}$) measured in nitrogen atmosphere

| Compound from example | $T_{sub}$ [° C.] | Substrate | μ (cm$^2$V$^{-1}$s$^{-1}$)$^a$ | $I_{on}/I_{off}$ | $V_t$ (V) |
|---|---|---|---|---|---|
| 1 | 70 | OTS | 1.12 ± 0.10 (1.26)$^b$ | (2.2 ± 0.9) × 10$^7$ | 15 ± 2 |
| 2 | 50 | OTS | 0.65 ± 0.16 (0.85) | (2.2 ± 0.8) × 10$^6$ | 29 ± 4 |
|   | 50 | Bare | 0.70 ± 0.09 (0.86) | (5.3 ± 1.3) × 10$^5$ | 20 ± 1 |

$^a$The average values obtained for at least 3 devices.
$^b$The maximum mobility recorded.

TABLE 2

Field field-effect mobilities (μ), on/off ratios (Ion/Ioff), and threshold voltages (Vt) for compounds of formula (I.B) at various substrate temperatures ($T_{sub}$) measured in ambient air

| Compound from example | $T_{sub}$ [° C.] | Substrate | μ (cm$^2$V$^{-1}$s$^{-1}$)$^a$ | $I_{on}/I_{off}$ | $V_t$ (V) |
|---|---|---|---|---|---|
| 1 | 70 | OTS | 1.32 ± 0.10 (1.43)$^b$ | (5.3 ± 0.6) × 10$^7$ | 23 ± 2 |
| 2 | 50 | OTS | 0.61 ± 0.15 (0.80) | (1.9 ± 0.9) × 10$^6$ | 39 ± 4 |
|   | 50 | Bare | 0.75 ± 0.13 (0.91) | (3.8 ± 1.7) × 10$^6$ | 25 ± 2 |

$^a$The average values obtained for at least 3 devices.
$^b$The maximum mobility recorded.

II.2 Production of Semiconductor Substrates by Means of Solution-Shared Deposition Highly doped n-type Si (100) wafers (<0.004 Ωcm) were used as substrates. A 300 nm SiO$_2$ layer (capacitance per unit area Ci=10 nF/cm$^2$) as a gate dielectric was thermally grown onto the Si substrates. These wafers were cleaned in piranha solution, a 7:3 mixture of H$_2$SO$_4$ and H$_2$O$_2$ by volume, rinsed with deionized water, and then dried by N$_2$. The phenyltrichlorosilane (PTS)-treated surface on SiO$_2$/Si substrates were obtained by the following procedures: a cleaning SiO$_2$/Si substrate was immersed into a 3 wt % solution of PTS in toluene at 80° C. for overnight. Then, the substrates were rinsed with toluene, acetone, isopropanol, and dried with a steam of nitrogen. The contact angle of the PTS-treated SiO$_2$/Si substrates was approximately 70° C. The organic semiconductor thin films were deposited on SiO$_2$/Si substrates through solution-sheared methods. Solution-sheared thin films were prepared as described below: After drying these samples overnight at 70° C., 40 nm gold contacts were evaporated onto the films to fabricate devices with a 50 μm channel length (L), and a W/L ratio of approximately 20. The OTFT transfer and output characteristics were recorded in a N$_2$-filled glove box by using a Keithley 4200 semiconductor parametric analyzer (Keithley Instruments, Cleveland Ohio). For air-stability, the samples were also monitored as functions of time after exposing in air. If not stated to contrary, the devices have channel length parallel to the shearing direction.

Solution Shearing:

The compounds were dissolved in ortho-dichlorobenzene (5 or 10 mg ml$^{-1}$) and the solution was dropped on the wafer substrate placed on a hot spot. A hydrophobic SiO$_2$/Si wafer treated with PTS was placed on top of the solution drop. The top wafer was pulled over at a constant rate to apply shear on the solution. Shearing rate: 0.0086 mm/s; temperature: 126° C.

TABLE 3

Electric properties of compounds of fomula (I.B) deposited by the solution-shared method (solvent: ortho-dichlorobenzene)

| Compound from example | $T_{sub}$ [° C.] | Maximum mobility [cm$^2$V$^{-1}$s$^{-1}$] | Mobility [cm$^2$V$^{-1}$s$^{-1}$] | Average On/off | $V_t$ (V) |
|---|---|---|---|---|---|
| 1 | 126 | 6.50 × 10$^{-2}$ | (4.50 ± 2.16) × 10$^{-2}$ | 1.92 × 10$^5$ | −36 ± 13 |
| 2 | 126 | 2.16 × 10$^{-1}$ | (1.73 ± 0.60) × 10$^{-1}$ | 2.65 × 10$^5$ | −23 ± 10 |
| 4.3 | 126 | 3.99 × 10$^{-2}$ | (2.20 ± 1.20) × 10$^{-2}$ | 1.03 × 10$^5$ | 2 ± 3 |
| 4.4 | 126 | 5.66 × 10$^{-2}$ | (3.66 ± 0.56) × 10$^{-2}$ | 2.28 × 10$^4$ | 39 ± 4 |

$T_{sub}$ = T substrate
The average values were obtained from at least 4 devices.

Figure 1B:
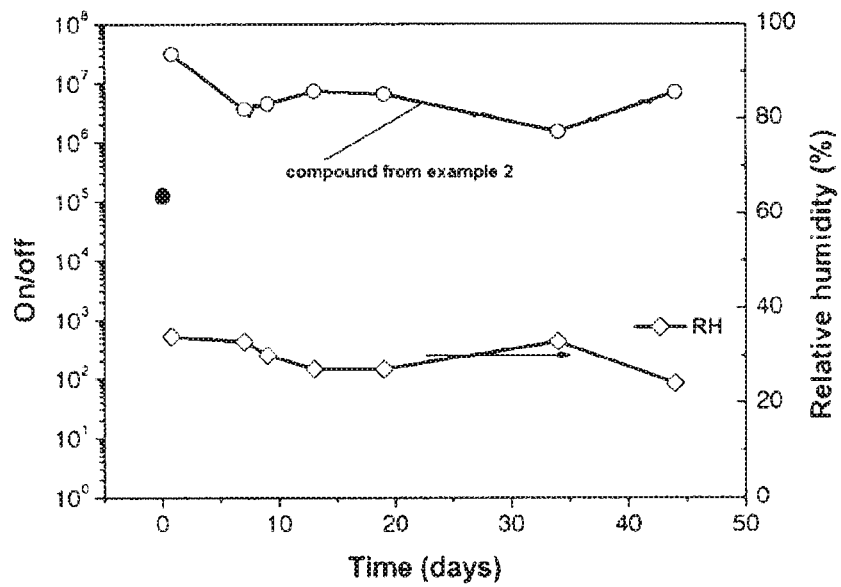
FIG. 1b is a graph of the on/off ratio of compound 2 in air depending on the relative humidity.
Figure 1C:
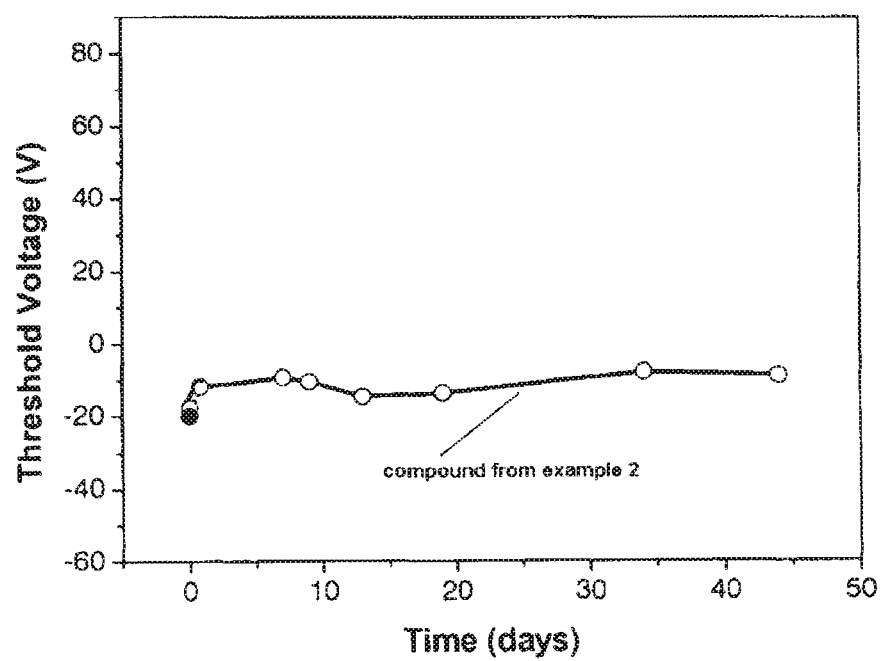
FIG. 1c is a graph of a correlation between the threshold voltage and time in air.

The air-stability testing of the studied molecules was monitored by measuring mobility, on/off ratios, and threshold voltages (Vt) as a function of time. The fluctuations of the electric properties of the OTFTs in air are often attributed to the influences of the relative humidity. The average mobility of 1, 2 and 4.3 decreased slightly from 4.50×10$^{-2}$, 1.73×10$^{-1}$, 2.20×10$^{-2}$ to 1.88×10$^{-2}$, 1.09×10$^{-1}$, 8.63×10$^{-3}$ cm$^{-2}$ V$^{-1}$ s$^{-1}$, respectively, after exposure to air for one and a half months. The fluctuations of the electric properties of OTFTs fabricated by solution-sheared deposition of the compound of example 2 in air depending on the relative humidity for a time of 50 days is shown in FIG. 1a (mobility) and FIG. 1b (on/off). FIG. 1c shows the correlation between threshold voltage and the time (50 days) in air. In the FIGS. 1a, 1b and 1c, the black filled circle at each occurrence corresponds to an electrical performance in a nitrogen glove box and RH means relative humidity.

The invention claimed is:

1. A compound of the formula (I.Ba)

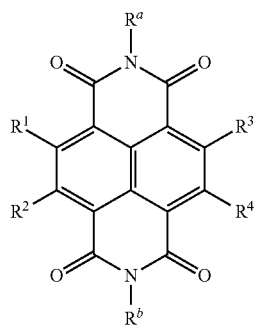

(I.Ba)

in which
R$^1$ and R$^3$ are each Cl and R$^2$ and R$^4$ are each hydrogen, or
R$^1$ and R$^4$ are each Cl and R$^2$ and R$^3$ are each hydrogen,
R$^a$ and R$^b$ are each independently 1H,1H-perfluoro-C$_2$-C$_{30}$-alkyl or 1H,1H,2H,2H-perfluoro-C$_3$-C$_{30}$-alkyl, wherein R$^a$ and R$^b$ are not each 1H,1H-perfluoro-C$_4$-alkyl.

2. The compound of the for a (I.Ba) according to claim 1, wherein R$^1$ and R$^4$ are each Cl and R$^2$ and R$^3$ are each hydrogen.

3. A process for preparing compounds of the formula (I.Ba) according to claim 1, the process comprising a2) reacting naphthalene-1,8:4,5-tetracarboxylic dianhydride with an amine of the formula Ra—NH$_2$ and optionally an amine of the formula Rb—NH$_2$ to obtain a compound of the formula (D)

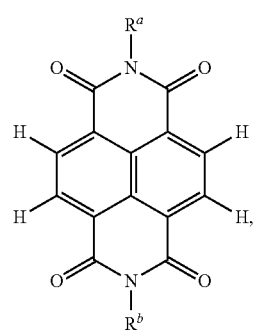

(D)

b2) subjecting the compound obtained in step a2) to a chlorination by reaction with chlorine in the presence of iodine as a catalyst.

4. The process as claimed in claim 3, wherein the chlorination of the compound of the formula (D) in step b2) is brought about by reaction with chlorine in chlorosulfonic acid and in the presence of catalytic amounts of iodine.

5. A compound of the formula (I.Ba)

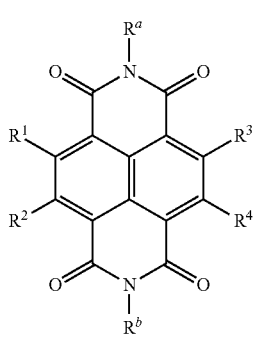

(I.Ba)

in which $R^1$ and $R^3$ are each Cl and $R^2$ and $R^4$ are each hydrogen; or $R^1$ and $R^4$ are each Cl and $R^2$ and $R^3$ are each hydrogen, and $R^a$ and $R^b$ are each 1H,1H-perfluoro-$C_4$-alkyl.

6. The compound according to claim 5, wherein $R^1$ and $R^3$ are each chlorine.

7. The compound to claim 5, wherein $R^1$ and $R^4$ are each chlorine.

\* \* \* \* \*

UNITED STATES PATENT AND TRADEMARK OFFICE
CERTIFICATE OF CORRECTION

PATENT NO. : 10,214,525 B2
APPLICATION NO. : 15/334743
DATED : February 26, 2019
INVENTOR(S) : Martin Koenemann et al.

It is certified that error appears in the above-identified patent and that said Letters Patent is hereby corrected as shown below:

On the Title Page

Column 1, item [54], Title, Line 2, "NAPTHALENETETRACARBOXYLIC" should read --NAPHTHALENETETRACARBOXYLIC--.

Page 2, Column 2, item (56), under other publications, Line 4, "Crysals" should read --Crystals--.

In the Specification

Column 1, Line 2, "NAPTHALENETETRACARBOXYLIC" should read --NAPHTHALENETETRACARBOXYLIC--.

Column 5, Line 37, delete "O." and insert --O,--.

Column 9, Line 16, "$C_3$-$C_5$-cycloalkyl" should read --$C_3$-$C_8$-cycloalkyl--.

Column 10, Line 60, "isooxazolyl," should read --isoxazolyl,--;

Column 10, Line 66, "$R^a$ und $R^b$" should read --$R^a$ and $R^b$--.

Column 13, Line 42, "5-pyrimiidylthio" should read --5-pyrimidylthio--.

Column 14, Line 51, "3-(rifluoromethyl)phenethyl" should read --3-(trifluoromethyl)phenethyl--.

Column 15, Line 23, "$C_3$-$C_{30}$-alkyl" should read --$C_3$-$C_{10}$-alkyl--.

Column 16, Line 10, "R" should read --$R^f$--.

Column 17, Line 28, "$R^a$" should read --$R^{a1}$--.

Signed and Sealed this
Twenty-ninth Day of October, 2019

Andrei Iancu
*Director of the United States Patent and Trademark Office*

CERTIFICATE OF CORRECTION (continued)
U.S. Pat. No. 10,214,525 B2

Column 19, Line 48, "n-$C_7F_{13}$" should read --n-$C_7$-$F_{15}$,--.

Column 22, Line 3, "dimid" should read --diimide--.

Column 34, Line 18, "Cl and $R^1$" should read --Cl and $R^2$--.

Column 37, Line 49, "$Cl_1SiOSiCl_3$," should read --$Cl_3SiOSiCl_3$--;

Column 37, Line 49, "$(CH_2)$" should read --$(CH_2)_6$--;

Column 37, Line 50, "ClSi" should read --$Cl_3Si$--.

Column 38, Line 6, "$Ta_2O$" should read --$Ta_2O_5$,--;

Column 38, Line 17, "$10^4$" should read --$10^{-4}$--;

Column 38, Line 60, "to 1000 nm" should read --10 to 1000 nm--.

Column 39, Line 63, "diethlyether" should read --diethylether--.

Column 41, Line 5, "to μm" should read --to 10 μm--.

Column 43, Line 22, "hexadeeachlorophthalocyanine" should read --hexadecachlorophthalocyanines--;

Column 43, Lines 23, "hexadeeachlorophthalocyanine" should read --hexadecachlorophthalocyanine--;

Column 43, Lines 24-25, "hexadeeachlorophthalocyanine" should read --hexadecachlorophthalocyanine--;

Column 43, Line 25, "hexadeeachlorophthalocyanine" should read --hexadecachlorophthalocyanine--.

Column 49, Line 45, "$Sio_2/Si$" should read --$SiO_2/Si$--;

Column 49, Line 67, "($l_d$) VS." should read --($l_d$) vx.--.

Column 51, Table 3, Line 1, "fomula" should read --formula--.

In the Claims

Column 52, Line 1, Claim 2, "for a" should read --formula--.

Column 53, Line 4, Claim 5, "hydrogen," should read --hydrogen;--.

Column 53, Line 8, Claim 7, after "compound" insert --according--.